United States Patent
Rubin

(10) Patent No.: US 11,628,267 B2
(45) Date of Patent: Apr. 18, 2023

(54) UNIVERSAL MEDICAL GAS DELIVERY SYSTEM

(71) Applicant: Medline Industries, LP, Springfield, IL (US)

(72) Inventor: Darren Rubin, Largo, FL (US)

(73) Assignee: Medline Industries, LP, Springfield, IL (US)

( * ) Notice: Subject to any disclaimer, the term of this patent is extended or adjusted under 35 U.S.C. 154(b) by 0 days.

(21) Appl. No.: 15/989,471

(22) Filed: May 25, 2018

(65) Prior Publication Data

US 2018/0272096 A1    Sep. 27, 2018

Related U.S. Application Data

(63) Continuation-in-part of application No. 14/952,272, filed on Nov. 25, 2015, now abandoned, which is a
(Continued)

(51) Int. Cl.
*A61M 16/08* (2006.01)
*A61M 11/00* (2006.01)
(Continued)

(52) U.S. Cl.
CPC ........ *A61M 16/0816* (2013.01); *A61M 11/00* (2013.01); *A61M 16/04* (2013.01);
(Continued)

(58) Field of Classification Search
CPC .......... A61M 16/0816; A61M 16/1005; A61M 39/10; A61M 16/06; A61M 16/04;
(Continued)

(56) References Cited

U.S. PATENT DOCUMENTS

| 1,009,031 A | 11/1911 | Millea |
| 1,977,847 A | 10/1934 | Gentle |

(Continued)

FOREIGN PATENT DOCUMENTS

| CA | 630903 | 11/1961 |
| DE | 3821154 | 10/1989 |

(Continued)

OTHER PUBLICATIONS

Intersurgical. Oxygen therapy flowmeters and adaptors poster with Sure-Loc Tubing. Version dated Feb. 1, 2015. Available online at https://www.intersurgical.com/content/files/71843/-1339154661.
(Continued)

*Primary Examiner* — Kendra D Carter
*Assistant Examiner* — Arielle Wolff
(74) *Attorney, Agent, or Firm* — Quarles & Brady LLP

(57) ABSTRACT

A first source of medical gas has a generally cylindrical male outlet with a cylindrical bore and a threaded outer cylindrical surface. A flexible cylindrical elastomeric medical gas tubing has an input end with a bushing making a flush abutment with the male outlet at the output orifice. An output end attaches to any of a plurality of medical gas utilizing devices, but preferably with a dampening disperser held in position in the space in the vicinity of a patient's nose and mouth. An annular flange of the input end bushing resides within a central cylindrical bored out region extending through the first end and nearly to the second end of a rotatable connector forming an interior surface of a connector with threads coupling with the threads of the male outlet. The second end is an annular abutment against the annular flange holding the input end tubing bushing against the outlet source and providing an airtight coupling. A gripping means is on the exterior surface of the connector.

36 Claims, 27 Drawing Sheets

Related U.S. Application Data continuation-in-part of application No. 14/214,974, filed on Mar. 16, 2014, now Pat. No. 9,199,052, which is a continuation-in-part of application No. 12/806,032, filed on Aug. 4, 2010, now Pat. No. 8,707,950.

(51) Int. Cl.

| | | |
|---|---|---|
| *A61M 16/04* | (2006.01) | |
| *A61M 16/06* | (2006.01) | |
| *A61M 39/10* | (2006.01) | |
| *A61M 16/10* | (2006.01) | |
| *A61M 16/14* | (2006.01) | |
| *A61M 16/00* | (2006.01) | |

(52) U.S. Cl.
CPC ........ *A61M 16/06* (2013.01); *A61M 16/1005* (2014.02); *A61M 39/10* (2013.01); *A61M 16/0605* (2014.02); *A61M 16/0808* (2013.01); *A61M 16/0875* (2013.01); *A61M 16/101* (2014.02); *A61M 16/14* (2013.01); *A61M 2016/0039* (2013.01); *A61M 2039/1033* (2013.01); *A61M 2039/1038* (2013.01); *A61M 2039/1077* (2013.01); *A61M 2202/025* (2013.01); *A61M 2202/0225* (2013.01); *A61M 2202/0241* (2013.01); *A61M 2202/0266* (2013.01); *A61M 2205/6081* (2013.01); *A61M 2206/14* (2013.01)

(58) Field of Classification Search
CPC  A61M 11/00; A61M 16/0808; A61M 16/101; A61M 16/0605; A61M 2206/14; A61M 2205/6081; A61M 2202/0266; A61M 2202/025; A61M 2202/0241; A61M 2202/0225; A61M 2016/0039; A61M 16/0875; A61M 2039/1033; A61M 16/14; A61M 2039/1077; A61M 2039/1038; B05B 3/026; B05B 3/028; A62C 33/04; A62C 31/00; A62B 9/04; F16L 19/02; F16L 47/04

See application file for complete search history.

(56) References Cited

U.S. PATENT DOCUMENTS

| | | | |
|---|---|---|---|
| 2,017,362 A | | 10/1935 | Werder |
| 2,050,647 A | | 8/1936 | Carter |
| 3,674,290 A | | 7/1972 | Mcnally |
| 3,799,589 A | | 3/1974 | Boelkins |
| 3,831,983 A | | 8/1974 | Stickler |
| 3,984,133 A | | 10/1976 | Bird |
| 4,073,512 A | | 2/1978 | Vian et al. |
| 4,106,505 A | | 8/1978 | Salter et al. |
| 4,133,312 A | | 1/1979 | Burd |
| 4,266,815 A | * | 5/1981 | Cross ............ F16L 47/16 604/905 |
| 4,446,863 A | | 5/1984 | Rubin et al. |
| 4,484,769 A | | 11/1984 | Lacey |
| 4,586,733 A | | 5/1986 | Anderson, Jr. |
| 4,685,456 A | | 8/1987 | Smart |
| 4,782,832 A | | 11/1988 | Trimble et al. |
| 4,824,145 A | | 4/1989 | Carlsson |
| 4,852,563 A | | 8/1989 | Gross |
| 4,969,879 A | * | 11/1990 | Lichte ............ A61M 39/10 285/319 |
| 4,981,586 A | | 1/1991 | Bartholomew |
| 5,024,419 A | | 6/1991 | Mulvey |
| 5,033,777 A | | 7/1991 | Blenkush |
| 5,062,420 A | | 11/1991 | Levine |
| 5,071,413 A | * | 12/1991 | Utterberg ............ A61M 5/162 604/533 |
| 5,176,415 A | | 1/1993 | Choksi |
| 5,188,609 A | | 2/1993 | Bayless et al. |
| 5,284,134 A | | 2/1994 | Vaughn et al. |
| 5,392,808 A | | 2/1995 | Pierce |
| 5,456,676 A | | 10/1995 | Nelson et al. |
| 5,466,017 A | | 11/1995 | Szabo et al. |
| 5,474,060 A | | 12/1995 | Evans |
| 5,572,994 A | | 11/1996 | Smith |
| 5,573,280 A | | 11/1996 | Salter et al. |
| 5,575,282 A | | 11/1996 | Knoch et al. |
| 5,611,576 A | * | 3/1997 | Guala ............ A61M 39/10 285/332 |
| 5,622,393 A | | 4/1997 | Elbich et al. |
| 5,647,354 A | | 7/1997 | Lakhani et al. |
| 5,690,612 A | * | 11/1997 | Lopez ............ A61M 5/14 604/246 |
| 5,702,374 A | * | 12/1997 | Johnson ............ A61M 39/10 128/912 |
| 5,709,204 A | | 1/1998 | Lester |
| 5,772,257 A | | 6/1998 | Webb et al. |
| 5,787,879 A | | 8/1998 | Gibson |
| 5,797,627 A | | 8/1998 | Salter et al. |
| 5,921,586 A | | 7/1999 | Prassas et al. |
| 6,012,451 A | | 1/2000 | Palmer |
| 6,050,552 A | | 4/2000 | Loescher et al. |
| 6,227,579 B1 | | 5/2001 | Humphreys |
| 6,248,099 B1 | | 6/2001 | Bell |
| 6,250,688 B1 | | 6/2001 | Kirby |
| 6,287,289 B1 | | 9/2001 | Niedospial, Jr. |
| 6,437,316 B1 | | 8/2002 | Colman et al. |
| 6,450,166 B1 | | 9/2002 | McDonald et al. |
| 6,488,026 B2 | | 12/2002 | Lauer |
| 6,502,864 B1 | | 1/2003 | Savard |
| 6,508,807 B1 | | 1/2003 | Peters |
| 6,517,119 B2 | | 2/2003 | Thomas |
| 6,581,593 B1 | * | 6/2003 | Rubin ............ F16L 19/0286 128/911 |
| 6,588,412 B2 | | 7/2003 | Ferrara et al. |
| 6,591,858 B2 | | 7/2003 | Peterson |
| 6,595,207 B1 | | 7/2003 | McDonald et al. |
| 6,631,719 B2 | | 10/2003 | McDonald et al. |
| 6,651,663 B2 | | 11/2003 | Barnett et al. |
| 6,675,796 B2 | | 1/2004 | McDonald |
| 6,677,530 B2 | | 1/2004 | Blaha et al. |
| 6,691,707 B1 | | 2/2004 | Gunaratnam et al. |
| 6,698,427 B1 | | 3/2004 | Clowers |
| 6,729,333 B2 | | 5/2004 | Barnett et al. |
| D493,523 S | | 7/2004 | Barnett et al. |
| 6,823,869 B2 | | 11/2004 | Raje et al. |
| 6,837,238 B2 | | 1/2005 | McDonald |
| 6,843,513 B2 | * | 1/2005 | Guala ............ A61M 39/1011 285/332 |
| D502,261 S | | 2/2005 | Kopacko et al. |
| 6,854,772 B2 | | 2/2005 | Weller et al. |
| 6,860,270 B2 | | 3/2005 | Sniadach |
| 6,895,965 B2 | | 5/2005 | Scarberry et al. |
| 6,959,710 B2 | | 11/2005 | Barnett et al. |
| D515,697 S | | 2/2006 | Nakamura et al. |
| 7,004,168 B2 | | 2/2006 | Mace et al. |
| 7,089,941 B2 | | 8/2006 | Bordewick et al. |
| 7,104,491 B2 | | 9/2006 | Vinding |
| 7,108,293 B2 | | 9/2006 | Van Der Meijden et al. |
| 7,156,096 B2 | | 1/2007 | Landis |
| 7,234,732 B2 | | 6/2007 | Ball |
| 7,255,106 B2 | | 8/2007 | Gallem et al. |
| 7,270,348 B2 | | 9/2007 | Parrott |
| 7,303,367 B2 | | 12/2007 | Rode |
| 7,350,831 B2 | | 4/2008 | Shimizu |
| 7,374,318 B2 | | 5/2008 | Brooks et al. |
| 7,383,839 B2 | | 6/2008 | Porat et al. |
| D574,490 S | | 8/2008 | Patzer |
| 7,458,615 B2 | | 12/2008 | White et al. |
| 7,487,791 B1 | | 2/2009 | Bradley |
| 7,503,326 B2 | | 3/2009 | Martin |
| 7,513,901 B2 | | 4/2009 | Seifert et al. |
| 7,523,967 B2 | | 4/2009 | Steppe |
| 7,559,326 B2 | | 7/2009 | Smith et al. |
| 7,594,910 B2 | | 9/2009 | Butts et al. |
| 7,608,581 B2 | | 10/2009 | Hamilton et al. |

(56) References Cited

U.S. PATENT DOCUMENTS

| | | | |
|---|---|---|---|
| 7,618,072 B2 | 11/2009 | Funamura et al. | |
| 7,622,523 B2 | 11/2009 | Li et al. | |
| 7,640,932 B2 | 1/2010 | Curti et al. | |
| 7,665,465 B2 | 2/2010 | Radney | |
| 7,678,101 B2 | 3/2010 | Sage | |
| 7,784,766 B2 | 8/2010 | Guala | |
| 7,845,685 B2 | 12/2010 | Blivet et al. | |
| 7,896,401 B2 * | 3/2011 | Richards | A61M 16/208 285/386 |
| 7,926,856 B2 | 4/2011 | Smutney et al. | |
| 8,074,963 B2 | 12/2011 | Iacopetta | |
| 8,287,518 B2 | 10/2012 | Kitani et al. | |
| 8,316,845 B2 | 11/2012 | Tappehorn et al. | |
| D674,895 S | 1/2013 | Rubin | |
| 8,424,917 B2 | 4/2013 | Christodoulou et al. | |
| 8,657,626 B2 | 2/2014 | Duval et al. | |
| 8,707,950 B1 | 4/2014 | Rubin | |
| 8,708,375 B2 | 4/2014 | Knis et al. | |
| 8,777,931 B2 * | 7/2014 | Davis | A61M 39/10 285/332 |
| 8,960,727 B2 | 2/2015 | Kendrick | |
| 9,010,056 B2 | 4/2015 | Ben David | |
| 9,199,052 B2 | 12/2015 | Rubin | |
| 9,261,215 B2 | 2/2016 | Kieper | |
| 9,597,475 B2 | 3/2017 | McPhearson | |
| 9,668,431 B2 | 6/2017 | Turk et al. | |
| 9,808,612 B2 | 11/2017 | Gulliver et al. | |
| 9,903,371 B2 | 2/2018 | Row et al. | |
| 9,925,350 B2 | 3/2018 | Laing et al. | |
| 2002/0100479 A1 | 8/2002 | Scarberry et al. | |
| 2002/0117849 A1 | 8/2002 | Bailey | |
| 2002/0124845 A1 | 9/2002 | Lauer | |
| 2002/0148472 A1 | 10/2002 | Barnett et al. | |
| 2003/0019496 A1 | 1/2003 | Kopacko et al. | |
| 2003/0024533 A1 | 2/2003 | Sniadach | |
| 2003/0047188 A1 | 3/2003 | Mace et al. | |
| 2003/0196662 A1 | 10/2003 | Ging et al. | |
| 2003/0201639 A1 * | 10/2003 | Korkor | F16L 19/0237 285/81 |
| 2004/0002693 A1 | 1/2004 | Bright et al. | |
| 2004/0035431 A1 | 2/2004 | Wright | |
| 2004/0094158 A1 | 5/2004 | Barnett et al. | |
| 2004/0094160 A1 | 5/2004 | McDonald | |
| 2004/0130150 A1 | 7/2004 | Stark | |
| 2004/0140376 A1 | 7/2004 | Alexander et al. | |
| 2004/0256014 A1 | 12/2004 | Kato | |
| 2005/0051171 A1 | 3/2005 | Booth | |
| 2005/0124970 A1 | 6/2005 | Kunin et al. | |
| 2005/0150498 A1 | 7/2005 | McDonald | |
| 2005/0234428 A1 | 10/2005 | Spohn et al. | |
| 2006/0027236 A1 | 2/2006 | Barnett et al. | |
| 2006/0076018 A1 | 4/2006 | Barnett et al. | |
| 2006/0081243 A1 | 4/2006 | McDonald et al. | |
| 2006/0081248 A1 | 4/2006 | McDonald | |
| 2006/0196510 A1 | 9/2006 | McDonald et al. | |
| 2006/0243282 A1 | 11/2006 | Sackman et al. | |
| 2006/0284421 A1 | 12/2006 | Fonville et al. | |
| 2007/0055218 A1 | 3/2007 | Menn | |
| 2007/0272245 A1 | 11/2007 | Ripple et al. | |
| 2007/0273148 A1 | 11/2007 | Duquette et al. | |
| 2008/0004600 A1 | 1/2008 | Kitani et al. | |
| 2008/0103484 A1 | 5/2008 | Hishikawa et al. | |
| 2008/0103485 A1 | 5/2008 | Kruger | |
| 2008/0110463 A1 | 5/2008 | Hajgato et al. | |
| 2009/0062776 A1 | 3/2009 | Funamura et al. | |
| 2009/0084385 A1 | 4/2009 | Lang | |
| 2009/0133697 A1 | 5/2009 | Kwok et al. | |
| 2009/0204080 A1 | 8/2009 | Balteau et al. | |
| 2009/0220298 A1 | 9/2009 | Gun | |
| 2009/0243281 A1 | 10/2009 | Seifert et al. | |
| 2009/0293975 A1 | 12/2009 | Iacopetta | |
| 2009/0318896 A1 | 12/2009 | Weststrate et al. | |
| 2009/0320851 A1 | 12/2009 | Selvarajan et al. | |
| 2010/0018535 A1 | 1/2010 | Chimenti et al. | |
| 2010/0020529 A1 | 1/2010 | Brooks et al. | |
| 2010/0030194 A1 | 2/2010 | Yokota et al. | |
| 2010/0084858 A1 | 4/2010 | Park | |
| 2010/0137729 A1 | 6/2010 | Pierry et al. | |
| 2010/0148500 A1 | 6/2010 | Uehara et al. | |
| 2010/0176584 A1 | 7/2010 | Ito et al. | |
| 2010/0201124 A1 | 8/2010 | Duquette et al. | |
| 2011/0006514 A1 | 1/2011 | Li et al. | |
| 2011/0023875 A1 | 2/2011 | Ledwith | |
| 2011/0112482 A1 | 5/2011 | Redd | |
| 2011/0203582 A1 | 8/2011 | Hacke et al. | |
| 2011/0298209 A1 * | 12/2011 | Nguyen | A61M 39/10 285/321 |
| 2012/0055485 A1 | 3/2012 | Anthony | |
| 2012/0117784 A1 | 5/2012 | Collin et al. | |
| 2012/0191029 A1 | 7/2012 | Hopf et al. | |
| 2014/0319823 A1 | 10/2014 | Happich | |
| 2014/0378950 A1 | 12/2014 | Chiu | |
| 2015/0151071 A1 | 6/2015 | Von Moger et al. | |
| 2015/0276111 A1 | 10/2015 | Ira et al. | |
| 2015/0335874 A1 | 11/2015 | Phillips et al. | |
| 2016/0003393 A1 | 1/2016 | Frame et al. | |
| 2016/0074610 A1 | 3/2016 | Rubin | |
| 2016/0082218 A1 | 3/2016 | Lau et al. | |
| 2016/0084287 A1 | 3/2016 | Daykin | |
| 2016/0354594 A1 | 12/2016 | Uehara et al. | |
| 2017/0007792 A1 | 1/2017 | Nye | |
| 2017/0182306 A1 | 6/2017 | Swantner | |
| 2017/0241581 A1 | 8/2017 | Decker | |
| 2017/0307120 A1 | 10/2017 | Guest | |
| 2018/0000695 A1 | 1/2018 | Stroup | |
| 2018/0043125 A1 | 2/2018 | Bencke et al. | |
| 2020/0038617 A1 | 2/2020 | Varga | |

FOREIGN PATENT DOCUMENTS

| | | |
|---|---|---|
| DE | 4114765 | 11/1992 |
| DE | 19833181 | 1/2000 |
| WO | 2002096500 | 12/2002 |
| WO | 2016075579 | 5/2016 |

OTHER PUBLICATIONS

Vortran Medical. The Go2Vent. Webpage. Archived version dated Jan. 27, 2021. Available online at https://web.archive.org/web/20210127013949/https://lok-corporation.com/go2vent/.

Vyaire Medical. AirLife Open Mask. Webpage. Archived version dated Dec. 14, 2021. Available online at https://web.archive org/web/20211214151441/https://www.vyaire.com/products/airlife-open.

* cited by examiner

UNIVERSAL MEDICAL GAS DELIVERY SYSTEM

RELATED APPLICATION

The present application is a continuation-in-part of U.S. patent application Ser. No. 14/952,272 filed Nov. 25, 2015, which is a continuation-in-part of U.S. patent application Ser. No. 14/214,974 filed Mar. 16, 2014, now U.S. Pat. No. 9,199,052, which is a continuation-in-part of U.S. patent application Ser. No. 12/806,032 filed Aug. 4, 2010, now U.S. Pat. No. 8,707,950, the subject matter of which applications are incorporated herein by reference.

BACKGROUND OF THE INVENTION

Background of the Invention

Oxygen is perhaps the most common form of medical gas used by hospitals, clinics, doctor offices, nursing homes, and in homecare. Other types of medical gas include compressed air, oxygen, carbon dioxide, nitrous oxide, nitrogen, helium, and cyclopropane. U.S. Pat. No. 6,581,593 is limited to sources of oxygen gas and oxygen tubing; whereas, the present invention provides a universal medical gas delivery system to be used with all types of medical gas. Furthermore, the present invention also includes numerous other uses and improvements.

Over the years, numerous injuries and deaths have been reported as the result of medical gas mix-ups, which occur when a patient's tubing is connected to the wrong medical gas source and the patient consequently received the wrong type of medical gas. For instance, a patient's oxygen supply tubing may be mistakenly connected to a nitrogen source outlet. Color-coded fittings on both the medical gas tubing and the medical gas source (flow meter) outlet can avoid such errors. Sources and vessels of medical gas may be color-coded as follows: air, yellow; oxygen, green; carbon dioxide, gray; nitrous oxide, blue; nitrogen, black; helium, brown; and cyclopropane, orange. One purpose of this invention is to include color-coded tubing and fittings, such as the rotating nut, corresponding to the type of medical gas prescribed.

However, some caregivers and patients may be color blind. It is another aim of this invention to provide tubing and/or fittings that are labeled for the type of medical gas prescribed. Additionally, the labeling may include raised lettering, indicia, and/or Braille for people with blindness or visual impairment. The tubing and/or connector may also be made from glow-in-the-dark or translucent materials to improve visualization in dark-lit rooms. The tubing may also be illuminated by a light source, such as LEDs, and light may also be transmitted by fiber optic threads incorporated into the tubing, to aid visualization of the tubing system in dark-lit rooms, which provides an advantage over U.S. Pat. No. 7,374,318 and 2010/0020529 that describes a hook apparatus for lighting oxygen tubing.

Medical gas tubing, such as oxygen tubing, that do not come in contact with bodily fluids, are generally disposed of in regular garbage. As a result, each year, millions of units of medical gas supply tubing ends up in both landfills and incineration plants. An additional aim of this invention is to produce medical gas supply tubing from non-toxic materials or polymers that do not release toxins into the air or ground water. A further intention of the current invention is to produce medical gas supply tubing that is more readily degradable in the environment, and may include biodegradable materials and/or additives and/or swelling agents. Said materials may also dissolve with certain solvents. Such design should reduce the environmental impact of disposable tubing supplies.

Oxygen tubing is generally packaged as non-sterile tubing. A further aim of this invention is to manufacture medical gas supply tubing that is composed of radiation resistant materials such that it can be sterilized by radiation, such as by gamma radiation, as disclosed in U.S. Pat. No. 7,622,523. Heat resistant materials may also be employed so that tubing can be autoclaved for sterilization, especially if reused in conjunction with a respiratory machine, such as an anesthesia machine or mechanical ventilator. Furthermore, poor developing nations may need to reuse medical gas tubing supplies as availability of such supplies may be limited. Such sterilization can be important for reducing or preventing cross-contamination in immunocompromised patients. The medical gas tubing and/or connector may also be composed of, or coated with, anti-microbial materials to reduce subsequent contamination, as disclosed in U.S. Pat. No. 7,608,581.

The present invention also reduces contamination and cross-contamination to patient users, since it bypasses the need for supply tubing adapters, many of which are reused between patients stays in the hospital, and become dirty and contaminated when transported in coat pockets and dropped on the floor. With infectious bacteria becoming ever more antibiotic resistance, such as methicillin-resistant *Staphylococcus aureus* (MRSA), any means of limiting patient contamination is desirable. The present invention fulfills this need.

It is a further aim of this invention to prevent patients and/or caregivers from tripping over long medical gas supply tubing. One way to reduce slack is with self-coiling oxygen tubing, comprised of a series of helical coils or loops able to stretch and extend when pulled, and able to retract again when no force is applied, as disclosed in U.S. Pat. No. 4,685,456. If tubing is not self-coiling, then a tubing reel may be used to wind and unwind this tubing to reduce excess tubing length when needed, as disclosed in U.S. Pat. Nos. 5,392,808; 6,591,858; 7,104,491; and 7,487,791 and 2006/0243282.

A swivel element and/or swivel adapter may also be employed to release tension from twisted tubing, as disclosed by U.S. Pat. Nos. 5,284,134; 5,573,280; and 5,797,627. A clip may also be employed to help hold the medical gas tubing onto a patient's clothing, bed, wheelchair, or chair, as disclosed by U.S. Pat. No. 5,188,609.

Medical gas tubing can provide medical gas to a variety of different medical gas utilizing devices. Most often medical gas tubing includes a nasal cannula or a face mask for delivery of gases directly to, or in the vicinity of, the nose and/or mouth. Sometimes the medical gas will dry the patient's airways, and so, a humidifier jar, such as described by U.S. Pat. No. 6,050,552 may be used to humidify the gas. When there is too much humidification, a condensation trap may also be placed in the supply tubing line to capture this excess moisture.

For instance, U.S. Pat. No. 4,106,505 describes a basic nasal cannula held on the head with over-the-ear tubing, while 2004/0035431 describes a nasal cannula with molded ear fittings for a better hold. Nasal cannulas may contain additional sampling tubes for monitoring patient breathing via an electronic detector, such as U.S. Pat. Nos. 7,640,932 and 7,383,839, the latter of which also contains an oral scoop. U.S. Pat. No. 5,575,282 describes an oxygen distributor with both mouth and nose delivery ports and a whirler to provide helical flow of gas.

An alternative to nasal cannulas, which enter the patient's nostrils, are face masks. Face masks come in all shapes and sizes. Some nasal masks only cover the nose, such as U.S. Pat. Nos. 6,651,663; 6,729,333; 6,959,710; D493,523; D502,261; 2002/0148472; 2004/0094158; and 2006/0027236, which describe a triangular nasal mask with headgear attachment.

Other masks are larger and cover both the nose and mouth of the patient. U.S. Pat. Nos. 7,004,168 and 2003/0047188 describe a face mask for oral and nasal delivery and gas sampling. Face masks can be held in place with elastic straps, or can be held in place with a headgear, which sometimes resembles a phone headset, and often contains arms and joints, which may be adjustable like the mask described by U.S. Pat. No. 7,089,941 and D515,697.

Because masks rest on the face, patients often complain of discomfort. Some have tried to invent masks that are more comfortable. U.S. Pat. Nos. 6,895,965; 20020100479; 20030019496; and 20060076018 describe a face mask with a rotatable elbow, and mask seal with cushion, the seal being formable and customizable to contour the face. Likewise, U.S. Pat. No. 6,698,427 describes a fabric comfort ring for patient medical masks, while 2010/0018535 describes a gel cushion for a mask that forms to the face, and 2005/0051171 describes a nose breathing mask with silicone wax molded for comfort.

For caregiver access to the patient's nose and/or mouth, such as for a patient drinking through a straw or for suctioning of patient fluids, some masks contain one or more access ports or regions, including 2009/0084385; 2003/0024533; and 2008/0110463, the latter of which attaches to a nebulizer to provide aerosol therapy. U.S. Pat. No. 7,255,106 also describes an inhalation mask for use with nebulizer, but unlike 2008/0110463, it does not provide helical flow. Other face masks may contain an exhaust filter, such as described by U.S. Pat. No. 7,503,326. Other masks may be adapted to contain gas supply tubing that extends through the patient's nose and mouth for mechanical ventilation, such as U.S. Pat. No. 6,860,270 describes a face mask for mechanical ventilation that consists of an oral tube and a nasal tube that extends into the intubated patient.

U.S. Pat. Nos. 6,450,166; 6,595,207; 6,631,719; 6,675,796; and 6,837,238; and U.S. Pat. App. Nos. 20040094160; 20050150498; 20060081243; and 20060081248 describe a lightweight oxygen delivery system comprising a baffle to diffuse oxygen which can be delivered to a space in the vicinity of the patient's nose and mouth, when held in position by a boom, or a face mask, but contains a number of cumbersome plastic components, and its tubing, in and of itself, does not have the ability of being securely fastened to a source of oxygen, and so may pop off under high pressure or be pulled off inadvertently, and may also be limited by delivery of only oxygen gas to the patient.

However, many of these medical gas utilizing or delivery devices are still cumbersome, uncomfortable, inconvenient, and potentially unsafe. The present invention, along with its medical gas mask preferred embodiment, provides uncompromised safety and comfort, is easier to manufacture, and can replace many of the existing face masks and cannulas with a single device, to reduce inventory and save hospitals money.

Therefore, it can be appreciated that there exists a continuing need for a new and improved universal medical gas delivery system which can be used for coupling any of a plurality of different medical gas sources to a medical gas tube leading to any of a plurality of different medical gas utilizing devices. In this regard, the present invention substantially fulfills this need.

SUMMARY OF THE INVENTION

In view of the foregoing disadvantages inherent in the known types of medical gas delivery systems of known designs and configurations now present in the prior art, the present invention provides an improved universal medical gas delivery system. As such, the general purpose of the present invention, which will be described subsequently in greater detail, is to provide a new and improved universal medical gas delivery system and method which has all the advantages of the prior art and none of the disadvantages.

To attain this, the present invention essentially comprises a universal medical gas delivery system for coupling any of a plurality of different medical gas sources to a medical gas tube leading to any of a plurality of different medical gas utilizing devices. First provided is a first source of medical gas. The first source comprises a generally cylindrical male outlet. The male outlet has an output orifice and an inner bore through which source medical gas is adapted to pass. The male outlet also has an outer cylindrical surface with threads.

Next provided is a flexible cylindrical elastomeric medical gas tubing. The gas tubing is of an extended length and has an inner diameter and outer diameter. The gas tubing also has a first input end and a remote second output end. The first input end further comprises a bushing that makes a flush abutment with the first outlet source of medical gas at the output orifice. The second output end is adapted to attach to any of a plurality of medical gas utilizing devices. An annular flange of the first input end bushing is adapted to reside within a bored out region of a connector thereby preventing the tubing/bushing from being separated from the connector.

The connector is rotatable and has a first opening at a first end and a second opening at a second end. The bored out region of the connector is central and generally cylindrical and extends through the first end and nearly to the second end forming an interior surface. The interior surface of the connector has threads and is adapted to couple with the threads of the male outlet source of medical gas. The second end opening of the connector has a diameter less than the diameter of the annular flange of the first input end tubing bushing. The second end of the connector serves as an annular abutment against the annular flange thereby holding the first input end tubing bushing against the first outlet source of medical gas when the connector is screwed on and also provides an airtight coupling.

Next provided is at least one user gripping means on the exterior surface of the connector. The gripping means assists a user in the coupling/screwing of the connector to the outlet source of medical gas. The gripping means is chosen from physical gripping means including, but not limited to, grooves, fingertip indentations, radially protruding flanges, angled surfaces and edges, curved surfaces and edges, surface bumps and friction-causing rough surfaces.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved universal medical gas delivery system which has all of the advantages of the prior art medical gas delivery systems of known designs and configurations and none of the disadvantages.

It is another object of the present invention to provide a new and improved universal medical gas delivery system which may be easily and efficiently manufactured and marketed.

It is further object of the present invention to provide a new and improved universal medical gas delivery system which is of durable and reliable constructions.

An even further object of the present invention is to provide a new and improved universal medical gas delivery system which is susceptible of a low cost of manufacture with regard to both materials and labor, and which accordingly is then susceptible of low prices of sale to the consuming public, thereby making such universal medical gas delivery system economically available to the buying public.

Even still another object of the present invention is to provide a universal medical gas delivery system for coupling any of a plurality of different medical gas sources to a medical gas tube leading to any of a plurality of different medical gas utilizing devices.

Lastly, it is an object of the present invention to provide a new and improved universal medical gas delivery system. A first source of medical gas has a generally cylindrical male outlet with a cylindrical bore and a threaded outer cylindrical surface. A flexible cylindrical elastomeric medical gas tubing has an input end with a bushing making a flush abutment with the male outlet at the output orifice. An output end attaches to any of a plurality of medical gas utilizing devices.

An annular flange of the input end bushing resides within a central cylindrical bored out region extending through the first end and nearly to the second end of a rotatable connector forming an interior surface of a connector with threads coupling with the threads of the male outlet. The second end is an annular abutment against the annular flange holding the input end tubing bushing against the outlet source and providing an airtight coupling. A gripping means is on the exterior surface of the connector.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
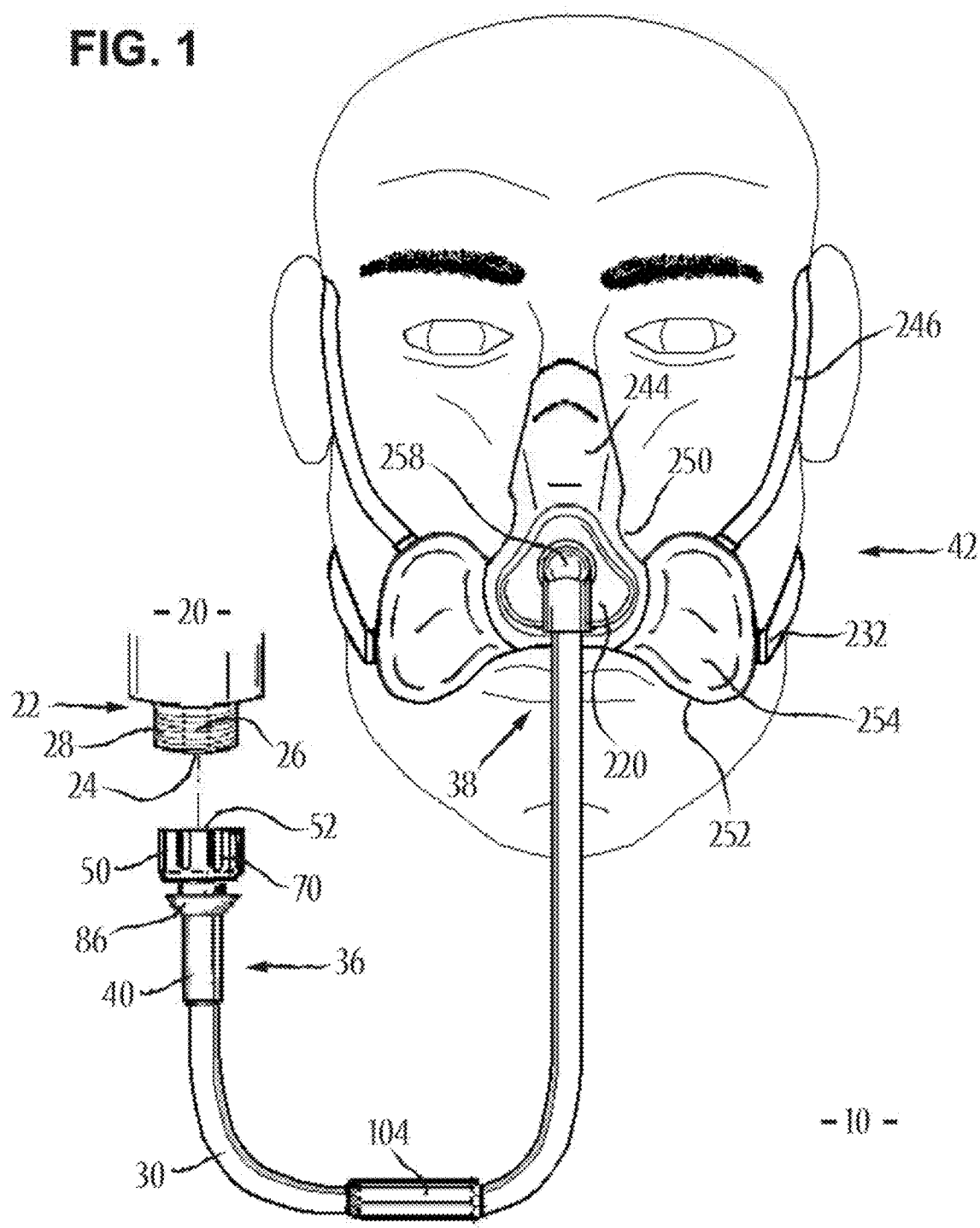
FIG. 1 is an improved universal medical gas delivery system consisting of medical gas tubing with rotatable threaded connector and tubing bushing, at first input end, that attaches to a source of medical gas (flow meter outlet), and is able to transfer medical gas to a respiratory gas utilizing device, at remote second output end, and in this figure, is shown with the third preferred embodiment of a dampening disperser in partial face mask housing, along with swivel elements.

With reference now to the drawings, and in particular to FIG. 1 thereof, the preferred embodiment of the new and improved universal medical gas delivery system embodying the principles and concepts of the present invention and generally designated by the reference numeral 10 will be described.

The present invention, the universal medical gas delivery system 10 is comprised of a plurality of components. Such components in their broadest context include a source of medical gas, a flexible cylindrical elastomeric medical gas tubing, a connector and a gripping means. Such components are individually configured and correlated with respect to each other so as to attain the desired objective.

The universal medical gas delivery system 10 is for coupling any of a plurality of different medical gas sources to a medical gas tube leading to any of a plurality of different medical gas utilizing devices. First provided is a first source of medical gas 20. The first source comprises a generally cylindrical male outlet 22. The male outlet has an output orifice 24 and an inner bore 26 through which source medical gas is adapted to pass. The male outlet also has an outer cylindrical surface with threads 28.

Figure 2:
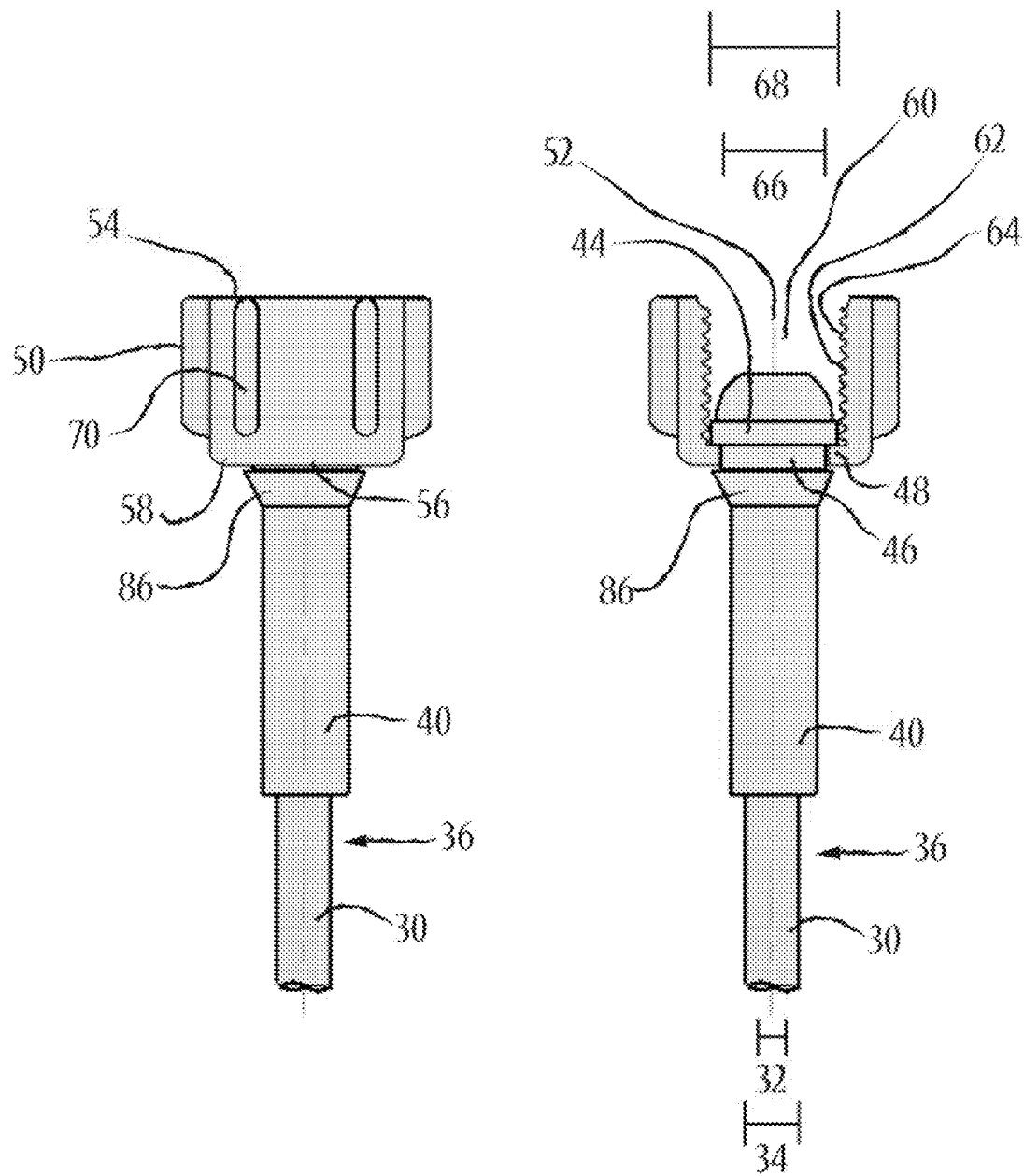
FIG. 2 is the first preferred embodiment of the threaded rotatable connector, with gripping means, and the medical gas tubing bushing, with annular flange and sliding-preventing (distance limiting) means; shown intact (left) and cross-section (right).
Figure 3:
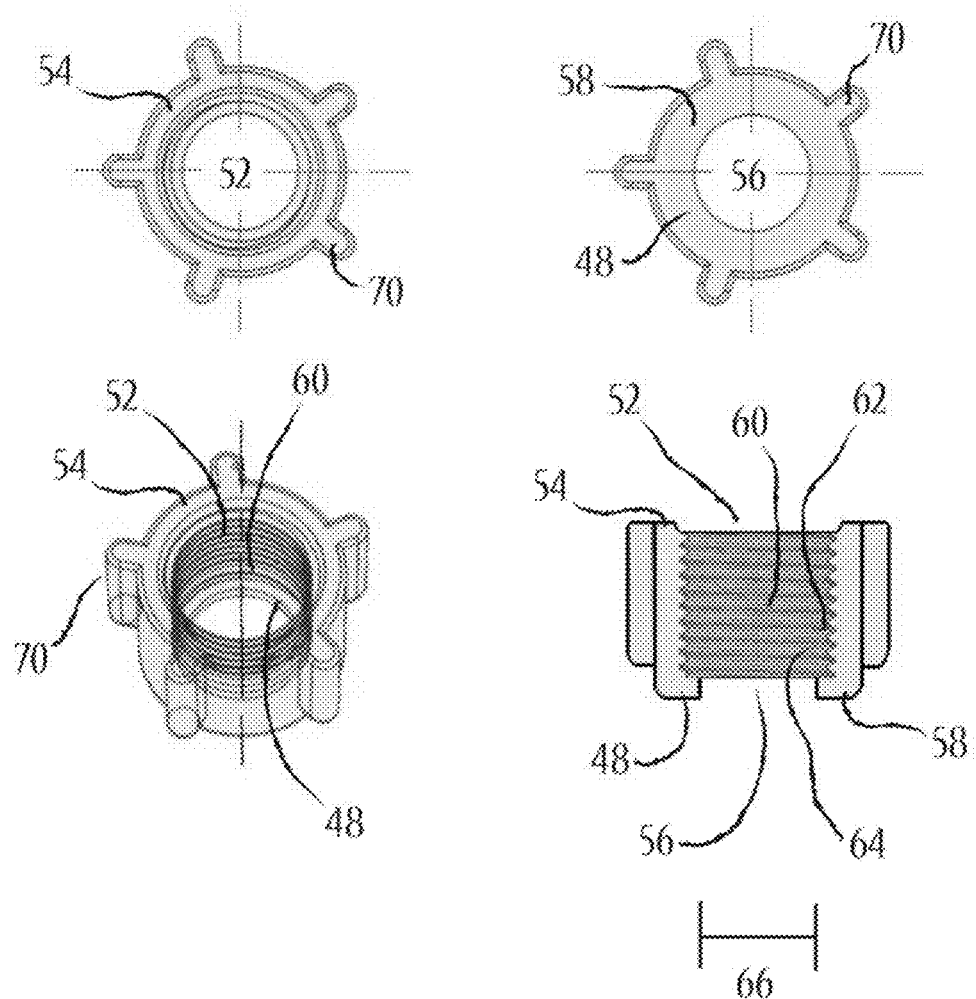
FIG. 3 provides greater detail of the threaded rotatable connector of the first preferred embodiment, viewed from the top down (top left of figure), bottom up (top right of figure), transparent three-dimensional view (bottom left of figure), and cross-section (bottom right of figure).

Next provided is a flexible cylindrical elastomeric medical gas tubing 30. The gas tubing is of an extended length and has an inner diameter 32 and outer diameter 34. The gas tubing also has a first input end 36 and a remote second output end 38. The first input end further comprises a tubing bushing 40 that makes a flush abutment with the cylindrical male outlet 22 of the source of medical gas at the output orifice 24. The remote second output end 38 is adapted to attach to any of a plurality of medical gas utilizing devices 42. In FIGS. 2 and 3, an annular flange 44 of the first input end tubing bushing 40 is adapted to reside within a bored out region 60 of a rotatable connector 50 thereby preventing the flexible cylindrical elastomeric medical gas tubing 30 and input end tubing bushing 40 from being separated from the connector.

The connector 50 is rotatable and has a first opening 52 at a first end 54 and a second opening 56 at a second end 58. The bored out region 60 of the connector is central and generally cylindrical 60 and extends through the first end 54 and nearly to the second end 58 forming an interior surface 62. The interior surface of the rotatable connector has threads 64 and is adapted to couple with the threads 28 of the cylindrical male outlet 22 of the source of medical gas 20. The second end opening 56 of the rotatable connector has a diameter 66 less than the diameter 68 of the annular flange 44 of the first input end 36 tubing bushing 40. The second end 58 of the connector serves as an annular abutment 48 against the annular flange 44 thereby holding the first input end tubing bushing 40 against the first outlet 22 source of medical gas when the connector 50 is screwed on and also provides an airtight coupling.

Next provided is at least one user gripping means 70 on the exterior surface of the connector. The gripping means assists a user in the coupling/screwing of the connector 50 to the outlet 22 source of medical gas 20. The gripping means 70 is chosen from physical gripping means including, but not limited to, grooves, fingertip indentations, radially protruding flanges, angled surfaces and edges, curved surfaces and edges, surface bumps and friction-causing rough surfaces.

At least one component of the first input end tubing bushing 40 is comprised of material chosen from a class of materials including, but not limited to, rigid materials, semi-rigid materials, semi-flexible materials, flexible materials and combinations of such materials thereof. Such materials include, but are not limited to, hard plastic, soft plastic, polymers, composites, polyethylene, polyvinyl chloride/PVC, acrylonitrile butadiene styrene/ABS, latex, silicone, metal and combinations thereof.

At least one component of the rotatable connector 50 is comprised of material chosen from a class of materials including, but not limited to, rigid materials, semi-rigid materials, semi-flexible materials, flexible materials and combinations of such materials thereof. Such materials include, but are not limited to, hard plastic, soft plastic, polymers, composites, polyethylene, polyvinyl chloride PVC, acrylonitrile butadiene styrene/ABS, latex, silicone, metal and combinations thereof.

In preferred embodiments of the invention, the connector 50 spins independently of the medical gas tubing 30 and screws onto the medical gas threaded male fitting 22 while the medical gas tubing 30 remains stationary. In this manner unnecessary twisting of the tubing is prevented.

In preferred embodiments of the invention, the medical gas tubing 30 cannot be disconnected from the medical gas threaded male fitting 22 once the threaded female connector 50 has been securely screwed onto this fitting. In this manner, the medical gas tubing 30 cannot be inadvertently pulled off and cannot be blown off as a result of gas pressure once the connector is coupled to this medical gas threaded male fitting 22.

Figure 4:
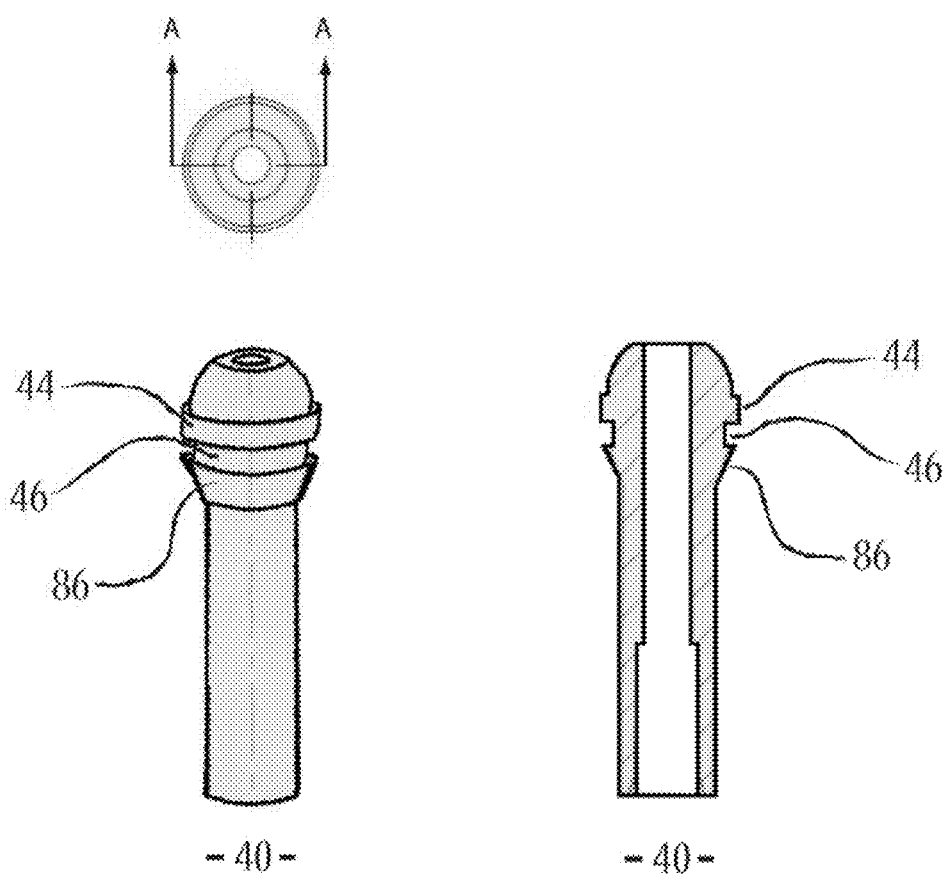
FIG. 4 provides greater detail of the medical gas tubing bushing in three-dimensions and cross-section, and also reveals the annular groove/track that the second end of the rotatable connector sits into to prevent the connector from sliding along the tubing.

In another preferred embodiment FIG. 4, the tubing end/bushing 40 further comprises an annular groove/indentation/track 46 adapted to house/contain at least some of the second end 58 walls/structure, the annular abutment 48 of the rotatable connector 50. The grooved track 46 allows the rotatable connector 50 to spin but prevents the rotatable connector from sliding along the axis 84 of the tubing to any appreciable extent. The grooved track 46 serves the purpose of the annular flange provided in other embodiments to prevent the connection from leaking gas and from the connector coming off the bushing. The tubing end bushing 40 has a general shape selected from the type of general shapes including, but not limited to, a cylindrical shape, curved shape, ball shape, semi-spherical shape, triangular shape, rectangular shape, trapezoid shape, bowl shape and any combination shape thereof.

Figure 5:
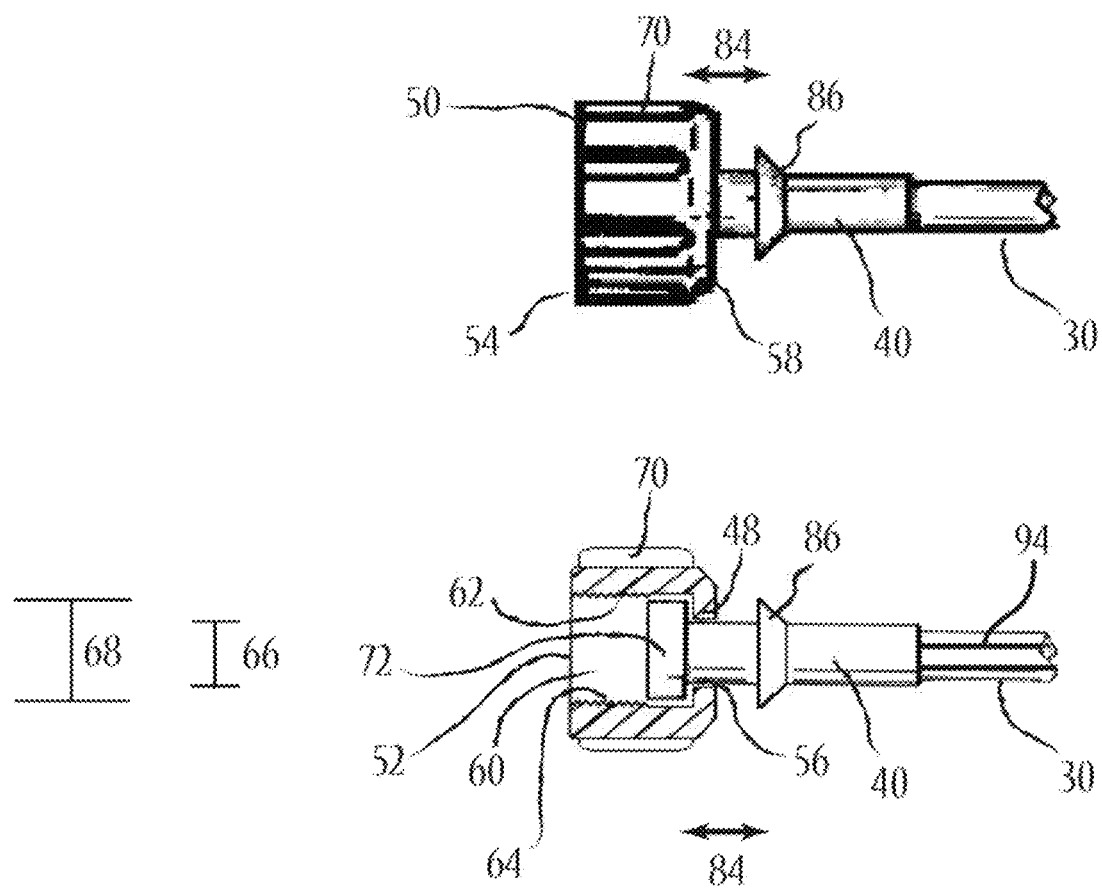
FIG. 5 is another first preferred embodiment of the threaded rotatable connector, with gripping means, and the medical gas tubing bushing; shown intact (top) and cross-section (bottom). In this embodiment, an elastomeric seal is provided at the bushing tip, and the connector is able to slide a limited distance to expose some of the bushing. The tubing is lumen tubing that contains reinforced, parallel channels to prevent tubing from kinking.

In another preferred embodiment of the invention FIG. 5, at least one seal 72 is provided to prevent gas leakage between the tubing connector 50 and the medical gas threaded male fitting outlet or inlet 22. The seal 72 is a fluidic mechanical seal selected from a class of mechanical seals including, but not limited to, washers, O-rings, X-rings, Q-rings, square rings and gaskets and further selected from mechanical seals that are removably placed within the medical gas delivery system and mechanical seals that are an integral component of the medical gas delivery system and any combinations thereof.

Figure 8:
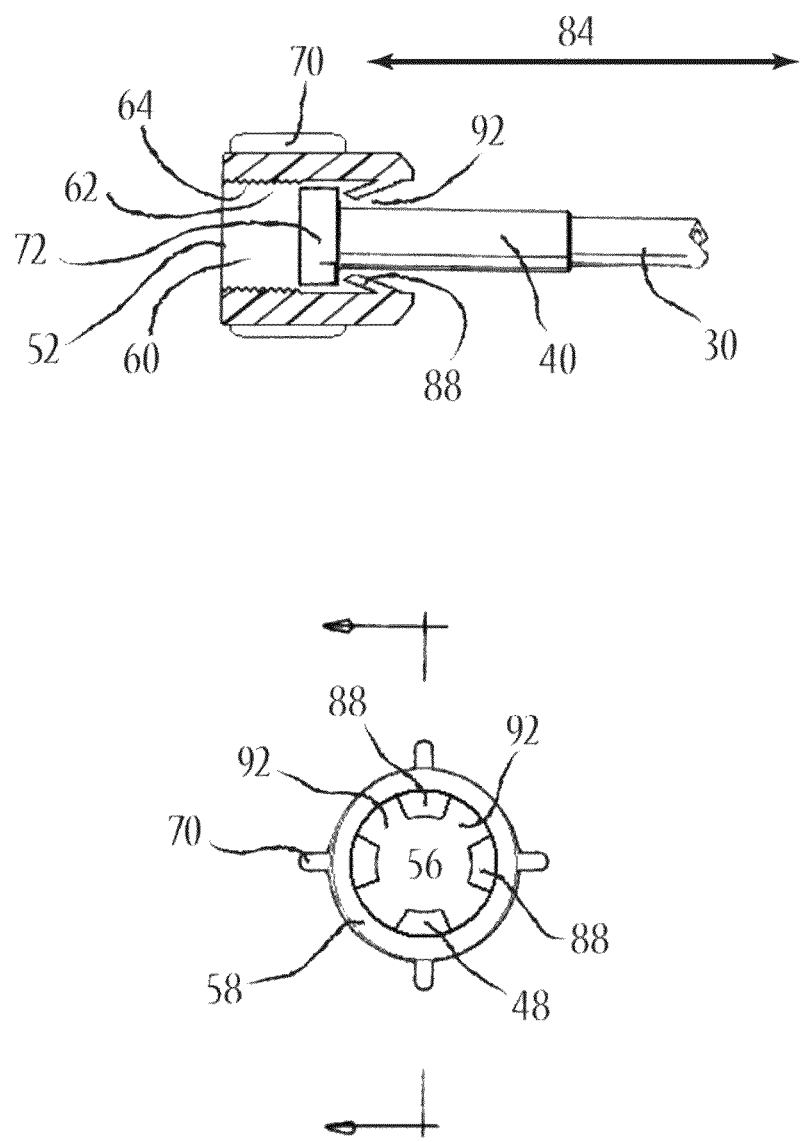
FIG. 8 is another first preferred embodiment of the threaded rotatable connector, with gripping means, and the medical gas tubing bushing shown cross-section (top). The second end of the rotatable connector has an annular recess, comprised of four flanges (bottom), which allows the connector to be pushed onto the bushing during manufacture, but cannot be taken off. There are no means of preventing the connector from sliding along the tubing, but these four flanges may catch on the tubing and reduce sliding by friction. The bushing can be fully exposed in this embodiment. An elastomeric washer comprises the annular flange of the tubing bushing.

In yet another preferred embodiment of the invention FIG. 8, the medical gas tubing 30 has an end that includes at least one elastomeric washer 72 to aid in providing an airtight seal between the connector 50 and the medical gas threaded male fitting 22. The elastomeric washer 72 can be integrally included as part of, in addition to, or instead of the annular flange 44.

Figure 6:
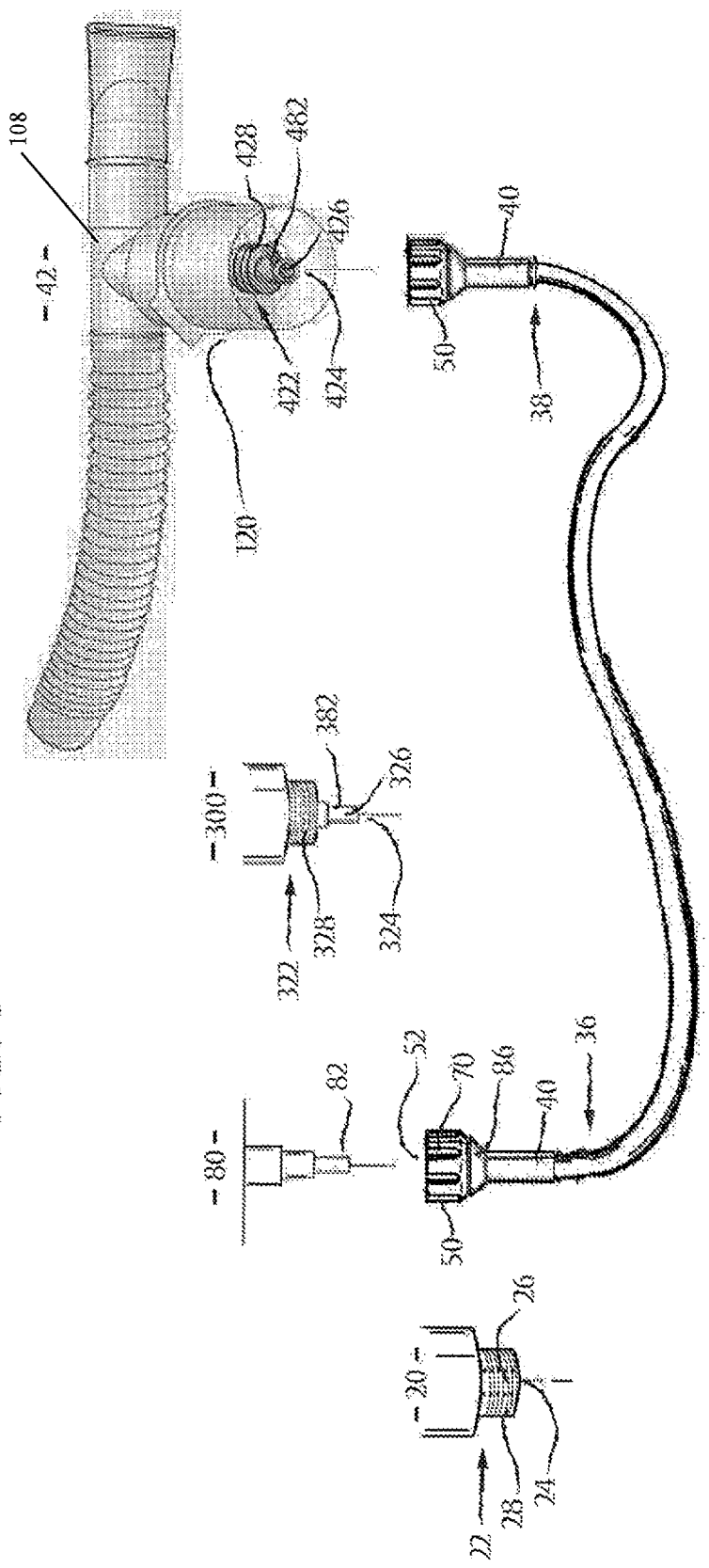
FIG. 6 is a second preferred embodiment of tubing with rotatable connectors on both ends of the tubing. The input end is able to connect to any of three different medical gas source outlets, two of which would be secure. The first outlet is a threaded, cylindrical male outlet allowing the connector to screw on; while the second outlet is a barbed stem (or nipple) that the tubing bushing can push onto. The third outlet is a new hybrid outlet according to the invention with a cylindrical male outlet allowing the connector to screw on securely, and also with a small stem (or nipple) that can simultaneously insert into the tubing bushing. The rotatable connector is also found on the output terminal of the tubing, allowing it to connect to a respiratory gas utilizing device, such as a nebulizer (as shown) with a threaded male medical gas delivery inlet/fitting.

In another preferred embodiment of the invention FIG. 6, the universal medical gas delivery system has a second/alternate source of medical gas 80. The second source of medical gas has an output end 82, nipple, nipple and nut adapter, barbed outlet, tubular outlet, of a reduced diameter with an axial inner bore through which source medical gas is adapted to pass. The reduced output end 82 is adapted to couple within the first input end 36 of the medical gas tubing/bushing 40 and allow the medical gas to pass from the source 80 to the tubing 30. The rotatable connector 50 is adapted to be used to help the user grip and push/pull on the tubing end to force the tubing first input end bushing 40 onto and over the nipple outlet 82 more tightly.

A third/alternate source of medical gas 300 is also shown in FIG. 6 having a medical gas delivery outlet/fitting according to the invention comprising an at least one at least partially threaded/at least partially cylindrical male medical gas outlet 322 with an at least one output orifice 324 and an inner bore 326 through which medical gas is adapted to pass and an outer cylindrical surface having threads 328 able to couple with the threads of a female rotatable connector 50 of a medical tubing input end 36 of a medical gas tubing 30 as the rotatable connector 50 is screwed on to the partially threaded/at least partially cylindrical male medical gas outlet 322. This medical gas delivery outlet/fitting further has a proximal tubular "nipple" portion 382 extending from the at least one at least partially threaded/at least partially cylindrical male medical gas outlet 322; the proximal tubular "nipple" portion 382 is able to have a bushing 40 of the medical gas tubing 30 input end 36 pushed onto/over the proximal tubular "nipple" portion 382, simultaneously or alternatively to the screwing on of the female rotatable connector 50. In most instances, the act of screwing the female rotatable connector 50 onto the outlet 322 is what pushes the bushing 40 onto this nipple portion 382. Such a system can allow for high flow rates of medical gas.

In still another preferred embodiment FIG. 5, the rotatable connector 50 can be slid up and down, back and forth, along the axis 84 of the tubing 30. In this manner it is slid away to expose the tubing end bushing 40 during coupling of the tubing end with a rigid tubular "nipple" structure, such as the nipple of a second source of medical gas outlet 82 or the nipple of a respiratory device 42. In this embodiment, means 86 can be provided for limiting the distance that the rotatable connector can travel from the tubing end, so as to not travel too far. The means for limiting this sliding distance of the rotatable connector 50 along the tubing can be chosen from such distance limiting means including, but not limited to, a barrier, such as an annular flange, washer, O-ring, dimple, bump, clasp, groove and wedge, on or as part of the tubing and/or bushing and friction causing means including, but not limited to, rough surfaces, jagged or disjointed edges and alternate embodiment flanges 88 of the annular recess of the second end 58 of the rotatable connector 50 that catches the tubing 30.

In another preferred embodiment FIG. 2, the rotatable connector 50 cannot be slid up and down back and forth along the axis of the tubing. The means 86 provided for preventing the rotatable connector from sliding along the axis 84 of the tubing can be chosen from such distance limiting means including, but not limited to, at least one barrier, such as an annular flange, washer, O-ring, dimple, bump, clasp and wedge, on or as part of the tubing and/or first end bushing. Said barrier 86 is unable to pass through the opening 56 of the second end 58 of the rotatable connector 50.

Figure 7:
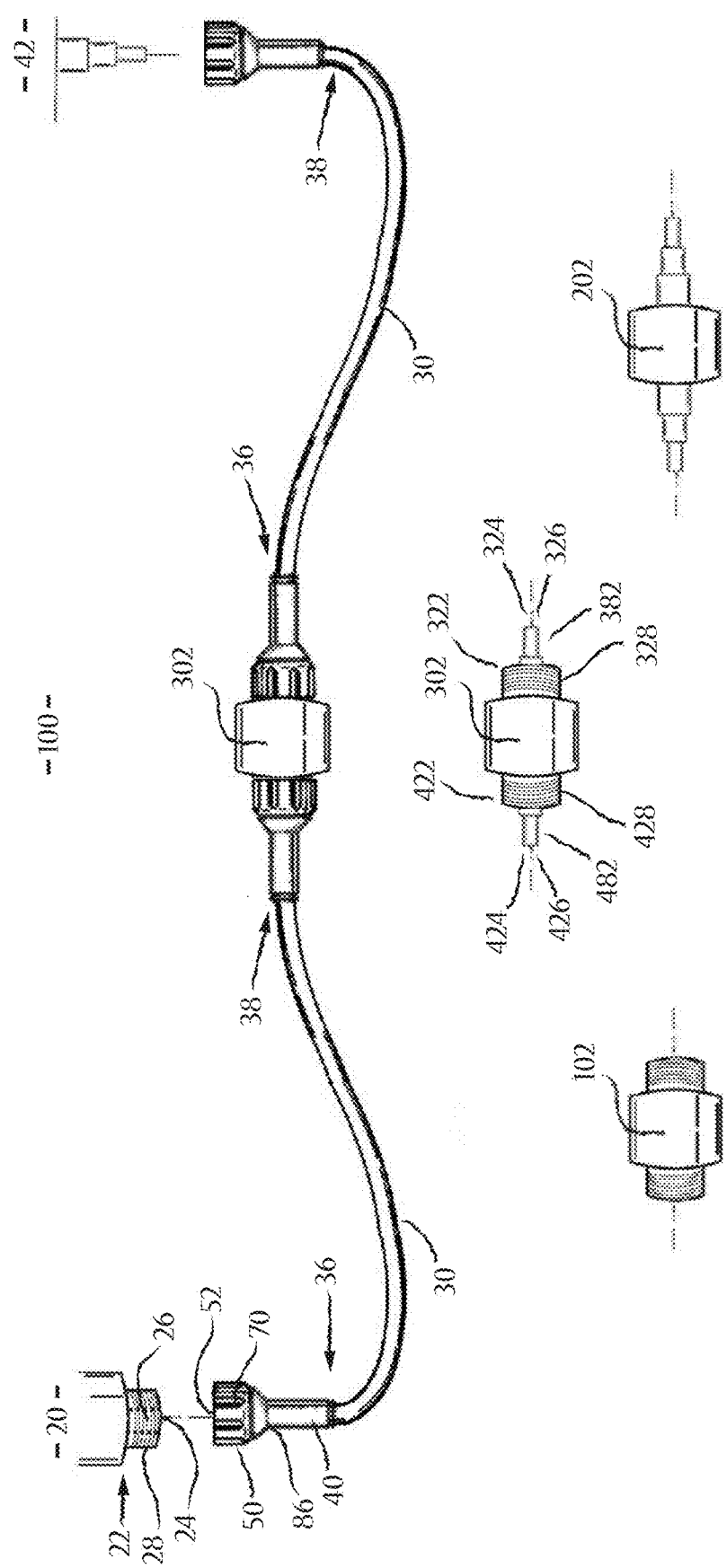
FIG. 7 is a second preferred embodiment with rotatable connectors on both ends of the tubing, thereby, allowing tubing to be connected in series using an adapter interface, such as to extend tubing length between the first source of medical gas and the respiratory gas utilizing device. Shown are three different adapters.

In other preferred embodiments FIGS. 6 and 7, the medical gas tubing 30 has at least one input terminal and at least one output terminal and at least one rotatable connector on the at least one input terminal and at least one output terminal.

In still other preferred embodiments FIGS. 6 and 7, the system is adapted to connect to at least one of a plurality of medical gas utilizing devices 42, including medical gas utilizing devices having an at least partially threaded/at least partially cylindrical male medical gas inlet 422 with an at least one input orifice 424 and a inner bore 426 through which medical gas is adapted to pass and an outer cylindrical surface having threads 428 able to couple with the threads of the female rotatable connector of the medical tubing output end/terminal as the connector is screwed on; and medical gas utilizing devices with a tubular "nipple" inlet of a reduced diameter with an axial bore which medical gas is adapted to pass, that an output end/terminal of the medical gas tubing can be pushed onto/over; or a combination thereof.

In another preferred embodiment FIG. 8, the rotatable connector 50 has an annular recess 92 of its second end 58 comprised of at least one flange 88 which allows the connector 50 to be pushed over the annular flange 44 of the tubing first end/bushing 40 during manufacture and assembly. The connector 50, however, cannot be pushed back over the annular flange 44 in the opposite direction. In addition, the at least one flange 88 of the connector can be angled non-perpendicular to the tubing and semi-flexible/bendable to achieve this association with the tubing.

The tubing provided is crush-resistant and kink-resistant as shown in FIG. 5. This type of tubing is otherwise known as "lumen tubing". This tubing contains one or more channels 94 along or within the tubing walls for reinforcing the tubing.

In second preferred embodiments FIG. 7, illustrated by the system identified by reference numeral 100, the universal medical gas delivery system is a plurality of systems are connected in series 100. These second preferred embodiments are for extending tubing length. These embodiments use an adapter 102, 202, or 302 chosen from adaptors including, but not limited to, an adapter 102 with at least two threaded male plugs that tubing threaded female connectors can screw onto, an adaptor 202 with at least two nipples that tubing can push onto, and an adaptor 302 with at least two threaded male plugs that tubing threaded female connectors can screw onto but also having a proximal nipple portion on each so that the tubing bushing pushes onto/over while the threaded connector is screwed on.

At least one swivel element/swivel adaptor 104 is provided FIG. 1 to release tension from twisted tubing as the element can be rotated. The swivel element can be chosen from a class of swivel elements including, but not limited to, ball joints, hollow cylindrical rod-like housings that contain another rod-like structure of smaller diameter inside of it and allowed to rotate within it and cylindrical rod-like structures able to turn freely within a support structure along with means are of preventing said swivel element from dissociating, chosen from such means including, but not limited to nuts, washers, pins and flanges.

Figure 9:
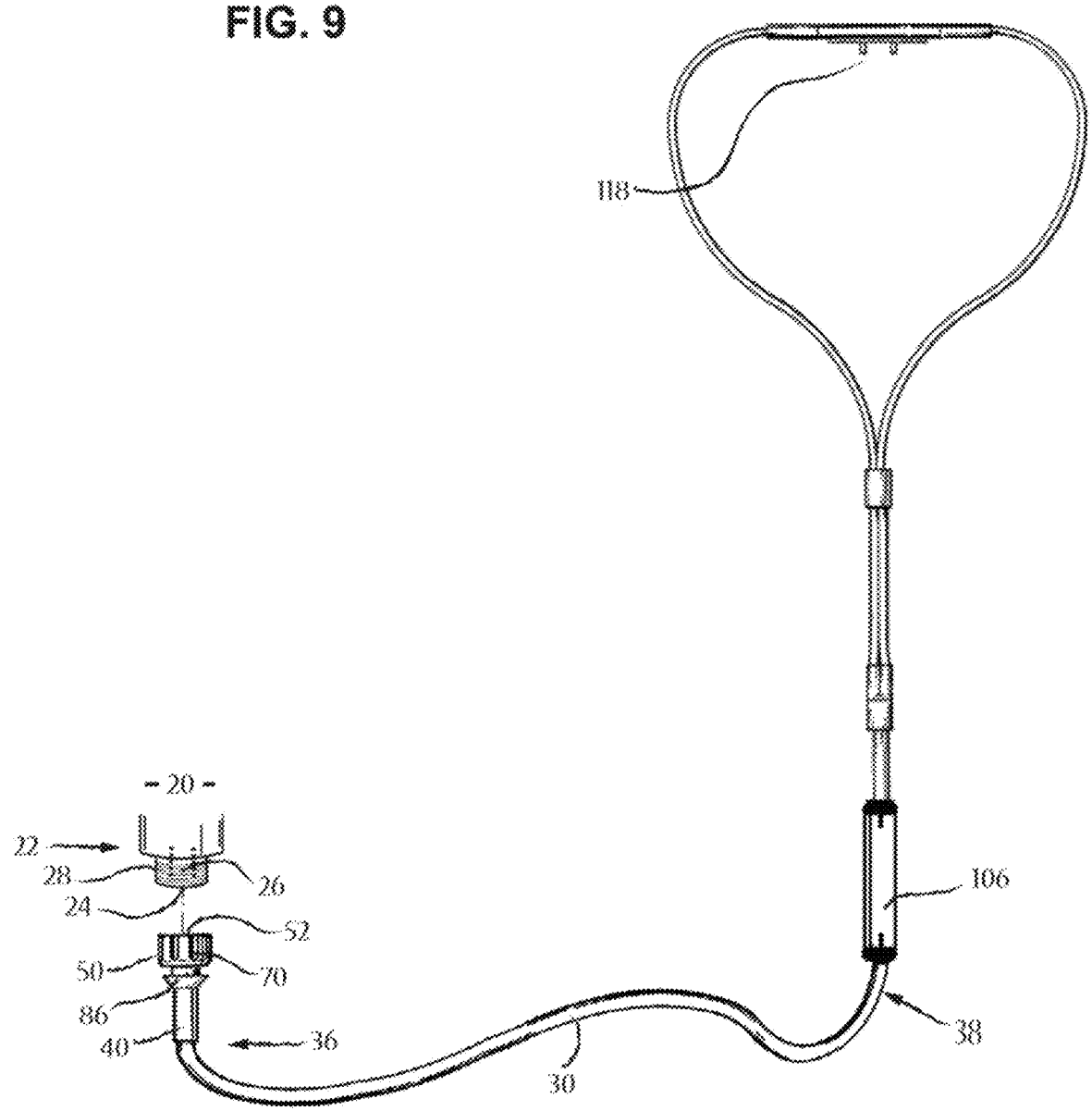
FIG. 9 is another second preferred embodiment that includes a condensation/water trap and a nasal cannula as a respiratory gas utilizing device.

In FIG. 9, further provided is a condensation trap tubing such as a water trap 106. Such trap functions to entrain moisture and humidity in the tubing.

Next an adapter/junction FIG. 6, such as an "X" and "Y" adapter and junction 108 is provided for connection to multiple sources of medical gas and to multiple respiratory devices/gas utilizing devices.

A quick disconnect element is next provided.

In second preferred embodiments, the medical gas supply tubing that is provided is self-coiling and comprised of a series of helical coils, loops able to stretch and extend when pulled and able to retract again on its own, when not pulled.

In second preferred embodiments, a tubing reel is provided to wind and unwind tubing to reduce excess tubing length as needed. This tubing reel may be manual and self-retracting.

In second preferred embodiments, a clip or swivel clip is provided. The clip functions to hold the gas tubing onto a patient's clothing, bed, wheelchair, or chair.

Figure 10:
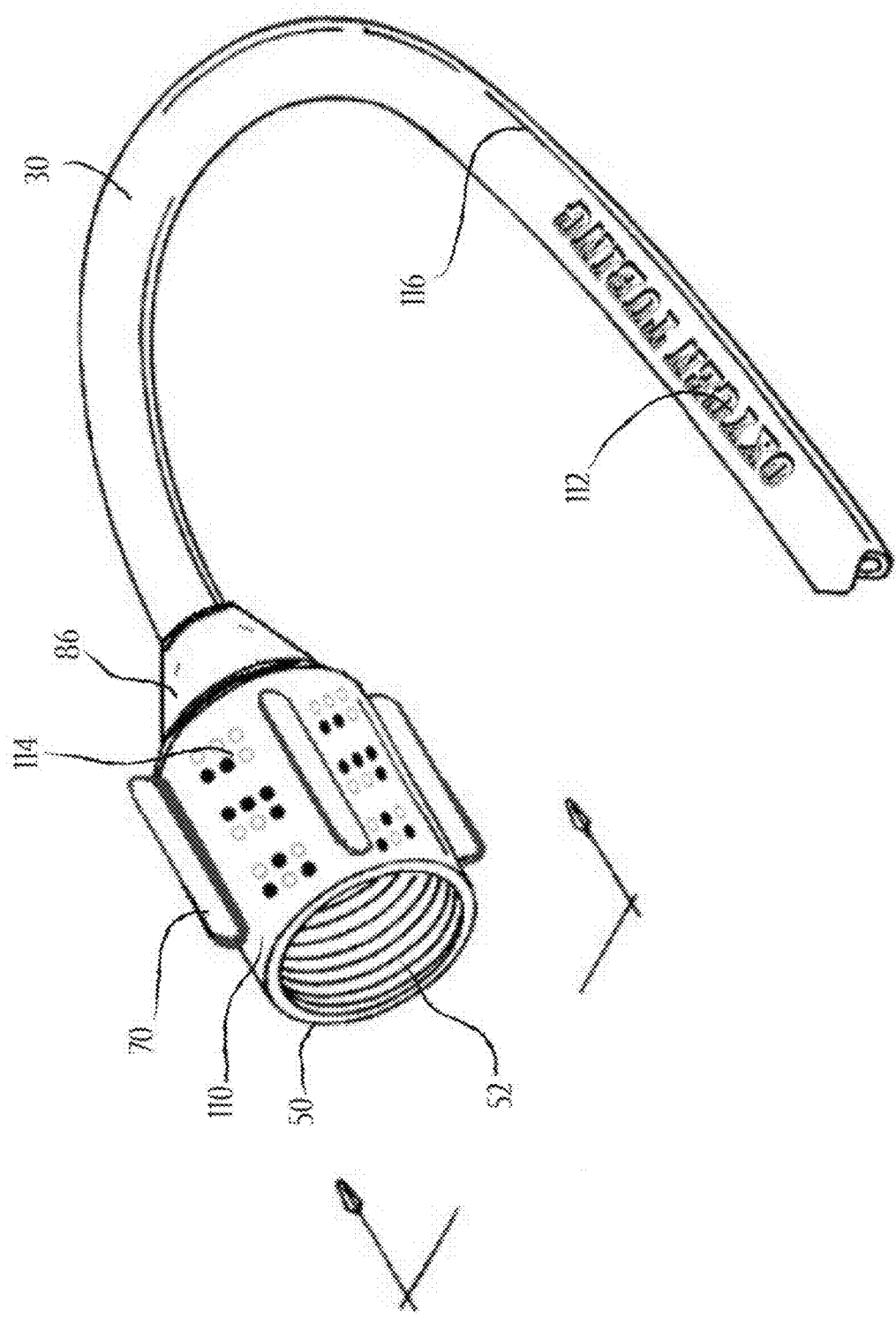
FIG. 10 is another second preferred embodiment that helps patients and health care workers utilize the correct gas source. The rotatable connector is color-coded, and includes raised Braille lettering to indicate which type of gas source to be used with this system. The tubing also includes glow-in-the-dark indicia that spells out the correct gas type. Also shown are fiber optic threads that provide tubing visibility at night, to prevent caregivers from tripping on the tubing.

Further, in second preferred embodiments, shown in FIG. 10, at least one component 110 that is color coded is provided for safety. The color coded component helps direct the user or care giver to the proper source of medical gas to avoid errors. Alternatively, at least one component is labeled to indicate the type of medical gas to be used. Labeling may be used for people with visual impairment including color blindness. The labeling can include raised lettering 112, indicia and/or Braille 114 to indicate the type of medical gas to be used. Also, alternatively, at least one component may be made from a glow-in-the-dark and/or translucent material, such as to aid visualization of the tubing system in dark-lit rooms. The tubing may be illuminated by a light source, such as LEDs and fiber optic threads 116 incorporated into the tubing.

In second preferred embodiments, the medical gas supply tubing and connector are comprised of and/or coated with anti-microbial materials to reduce microbial growth and contamination.

The at least one gas source is chosen from medical gas sources selected from a class of respiratory gas sources including, but not limited to, gas tanks, air compressors, oxygen concentrating devices, oxygen concentrators and wall-mounted flow meters; and capable of delivering medical gas chosen from the types of medical gases selected from a class of inhalable medical gases including, but not limited to, compressed air, oxygen, carbon dioxide, nitrous oxide, nitrogen, helium, carbon monoxide, nitric oxide, hydrogen sulfide, cyclopropane, other anesthesia gases and any combinations thereof.

The at least one respiratory apparatus is chosen from medical gas utilizing apparatuses selected from a class of respiratory gas utilizing devices including, but not limited to, nasal cannulas 118 (FIG. 9), face masks, venturi valves, venturi masks, mouthpieces, endotracheal catheters/endotracheal adapters, nebulizers/atomizers 120 (FIG. 6), aerosol masks, vaporizers, inhalers, aerosol holding chambers/spacers, spirometers, humidifier jars, humidifier devices, positive airway pressure devices, positive expiratory pressure devices, resuscitation bags also called artificial resuscitator, manual resuscitator, reanimation/resuscitation bag, "Ambu bag", gas mixing devices gas mixers, flow regulators, flow sensors, hyperbaric oxygen chambers, incubators, mechanical ventilators, ventilator line oxygen port adaptors, anesthesia machines/anesthesia ventilators, other respiratory line adapters and fittings and any combinations thereof. The invention also includes the above medical gas utilizing devices having at least one medical gas delivery inlet/fitting comprising an at least one at least partially threaded/at least partially cylindrical male medical gas inlet 422 with an at least one input orifice 424 and an inner bore 426 through which medical gas is adapted to pass and an outer cylindrical surface having threads 428 able to couple with the threads of a female rotatable connector 50 of a medical tubing output end 38 of a medical gas tubing 30 as the rotatable connector 50 is screwed on to the partially threaded/at least partially cylindrical male medical gas outlet 422. The medical gas delivery inlet/fitting of medical gas utilizing devices according to the invention may optional further have a proximal tubular "nipple" portion 482 extending from the at least one at least partially threaded/at least partially cylindrical male medical gas inlet 422; the proximal tubular "nipple" portion 382 is able to have a bushing 40 of the medical gas tubing 30 output end 38 be fit or pushed onto/over the proximal tubular "nipple" portion 482, including when the female rotatable connector 50 is being screwed securely onto the at least partially threaded/at least partially cylindrical male medical gas inlet 422. Other tubing without the threaded connector 50 may just push onto this nipple portion 482 non-securely. As shown in FIG. 6, the nebulizer/atomizer 120 has this at least partially threaded/at least partially cylindrical male medical gas inlet 422 along with the optional proximal tubular "nipple" portion 482 for a secure connection with the medical gas tubing 30 so that the nebulizer cannot be inadvertently pulled off or pop off from medical gas pressure/back pressure. This allows for use with a higher flow volume of medical gas, such as from the flow meter, so that better nebulizer/atomizer treatments can be had and/or with shorter nebulization/atomization treatment times.

The invention also includes a medical gas delivery outlet/fitting or adaptor 302 comprising an at least one at least partially threaded/at least partially cylindrical male medical gas outlet 322 with an at least one output orifice 324 and an inner bore 326 through which medical gas is adapted to pass and an outer cylindrical surface having threads 328 able to couple with the threads of a female rotatable connector 50 of a medical tubing input end 36 of a medical gas tubing 30 as the rotatable connector 50 is screwed on to the partially threaded/at least partially cylindrical male medical gas outlet 322. The medical gas delivery outlet/fitting or adaptor 302 further has a proximal tubular "nipple" portion 382 extending from the at least one at least partially threaded/at least partially cylindrical male medical gas outlet 322; the proximal tubular "nipple" portion 382 is able to have a bushing 40 of the medical gas tubing 30 input end 36 pushed onto/over the proximal tubular "nipple" portion 382. Other tubing without the threaded connector 50 may just push onto this nipple portion 382 non-securely.

The invention also includes a medical gas delivery inlet/fitting or adaptor 302 comprising an at least one at least partially threaded/at least partially cylindrical male medical gas inlet 422 with an at least one input orifice 424 and an inner bore 426 through which medical gas is adapted to pass and an outer cylindrical surface having threads 428 able to couple with the threads of a female rotatable connector 50 of a medical tubing output end 38 of a medical gas tubing 30 as the rotatable connector 50 is screwed on to the partially threaded/at least partially cylindrical male medical gas outlet 422. The medical gas delivery inlet/fitting or adaptor 302 further optionally has a proximal tubular "nipple" portion 482 extending from the at least one at least partially threaded/at least partially cylindrical male medical gas inlet 422; the proximal tubular "nipple" portion 382 is able to have a bushing 40 of the medical gas tubing 30 output end 38 pushed onto/over the proximal tubular "nipple" portion 482. Other tubing without the threaded connector 50 may just push onto this nipple portion 482 non-securely.

The invention also includes methods of using the medical gas delivery system according to the invention. A method is provided for preventing a medical gas utilizing device 42 from inadvertently being disconnected from a medical gas tubing 30 because of a medical gas pressure/back pressure, accidental pull, or a combination thereof. This method includes a step of coupling/screwing the medical gas tubing 30 output end 38 to an at least partially threaded/at least partially cylindrical male medical gas inlet 422 of the medical gas utilizing device 42 using a threaded rotatable connector 50 of the medical gas tubing 30; the method also includes a step of providing a medical gas from a medical gas source to the medical gas tubing 30 and then to the medical gas utilizing device 42. The method optionally including a step of increasing a medical gas flow rate of the medical gas into the medical gas tubing 30 in order to achieve greater medical gas delivery to the medical gas utilizing device 42, more rapid medical gas delivery to the medical gas utilizing device 42, a shorter treatment time of the medical gas utilizing device to a patient, or a combination thereof. In preferred embodiments, the medical gas utilizing device 42 according to this method is selected from an oxygen face mask, an at least partial oxygen face mask housing, a nasal cannula, an endotracheal tube or endotracheal tube oxygen port, a manual resuscitator/reanimation/ resuscitation bag, a positive airway pressure/positive expiratory pressure and or airway clearance device, a ventilator line or ventilator line oxygen port, or a nebulizer/atomizer 120.

In a primary embodiment according to the invention, the invention is a nebulizer/atomizer 120 having an at least partially threaded/at least partially cylindrical male medical gas inlet 422 to receive a threaded rotable connector 50 of the medical gas tubing 30 to perform the one or more methods according to the invention.

In preferred embodiments of this method, the step of coupling/screwing the medical gas tubing 30 output end 38 to an at least partially cylindrical male medical gas inlet 422 of the medical gas utilizing device 42 using a threaded rotable connector 50 of the medical gas tubing 30 is performed simultaneously to/or after having pushed a bushing 40 of the medical gas tubing 30 output end 38 at least partially onto/over a narrow proximal tubular "nipple" portion of the an at least partially threaded/at least partially cylindrical male medical gas inlet 422 of the medical gas utilizing device 42. The pushing is done by hand and or by the act of screwing the threaded connector 50 onto the medical gas inlet 422. (Other tubing without the threaded connector 50 may just push onto this nipple portion 482 non-securely.)

The invention also includes a method of preventing a medical gas utilizing device 42 from inadvertently being disconnected from a medical gas tubing 30 because of a medical gas pressure/back pressure, accidental pull, or a combination thereof. The method includes a step of coupling/screwing the medical gas tubing 30 output end 38 to an at least partially cylindrical male medical gas inlet 422 of the medical gas utilizing device 42 using a threaded rotable connector 50 of the medical gas tubing 30, simultaneously to/or after having pushed a bushing 40 of the medical gas tubing 30 output end 38 at least partially onto/over a narrow proximal tubular "nipple" portion of the an at least partially threaded/at least partially cylindrical male medical gas inlet 422 of the medical gas utilizing device 42. The pushing is done by hand and or by the act of screwing the threaded connector 50 onto the medical gas inlet 422. The method also includes a step of providing a medical gas from a medical gas source to the medical gas tubing 30 and then to the medical gas utilizing device 42. The method optionally including a step of increasing a medical gas flow rate of the medical gas into the medical gas tubing 30 in order to achieve greater medical gas delivery to the medical gas utilizing device 42, more rapid medical gas delivery to the medical gas utilizing device 42, a shorter treatment time of the medical gas utilizing device to a patient, or a combination thereof. In preferred embodiments, the medical gas utilizing device 42 according to this method is selected from an oxygen face mask, an at least partial oxygen face mask housing, a nasal cannula, an endotracheal tube or endotracheal tube oxygen port, a manual resuscitator/reanimation/ resuscitation bag, a positive airway pressure/positive expiratory pressure and or airway clearance device, a ventilator line or ventilator line oxygen port, or a nebulizer/atomizer 120.

Third preferred embodiments of the present universal medical gas delivery system invention (FIGS. 1, and 11A through 19C) are comprised of a dampening disperser that reduces the velocity of medical gas flowing from the source of medical gas to a space in the vicinity of the patient's nose and mouth, such as between the upper lip and the base of the nose, while generating vortices to mix the gases in the vicinity of the patient's nose and mouth. This allows for both nose breathing and mouth breathing of these gases. The dampening disperser releases medical gas in a way that causes at least some turbulence and negative interference to slow the velocities of the gas streams, to reduce full impact of gas flow with the patient's face. The interference can also cause angular momentum and circular motion to further enhance vortex formation and gas mixing. Vortex formation and gas mixing are important for clearing exhaled breath away from the patient and can also allow for mixing of medical gas with ambient air in approximately this same space. The interior walls of the dampening disperser, which contain at least one gas outlet nozzle that dispenses gas within/into the interior region of the dampening disperser, are concave cup-like in shape, and these walls can be angled to help focus and direct gas vortices toward the patient, such as towards the patient's mouth. The dampening disperser can be attached to a variety of different supports in communication with the patient's head to position the dampening disperser in the vicinity of the patient's nose and mouth. Different supports include that of an at least a partial face mask housing of full or partial face masks. Gas outlets of the dampening disperser can meet at a junction. The dampening disperser is connected to at least one medical gas tube. The medical gas tubing can be connected to the flow meter of at least one medical gas source, utilizing the rotatable rigid connector described herein. The rotatable rigid connector described herein can provide a safe and reliable connection to the medical gas source, that cannot be inadvertently pulled off, or shot off by pressure, such as when the flow meter is set to a high flow rate above 15 liters per minute. Therefore, with the present invention, the flow meter of the at least one source of medical gas can be safely adjusted from low flow rates to high flow rates, so that the fraction of an inspired medical gas, such as the fraction of inspired oxygen (FiO2), can be adjusted accordingly to accommodate the full range of a gas concentration for a patient's needs. For instance, the flow meter can be adjusted so that the present device can deliver a FiO2 within and beyond the range of 24% to 90%, with flow meter settings within and beyond 1 liter per minute to 40 liters per minute.

Third preferred embodiments may also allow access to the patient's mouth and nose through at least one of these at least one vent, aperture, cutaway, or gap of the mask. The lightweight and less cumbersome, open access feature of the preferred "open" face mask embodiment can prevent pressure build-up in the system and can allow for: the improved clearance of patient exhalation for nonrebreathing of carbon dioxide; better mixing of medical gas with ambient air; easier caregiver access to the patient's mouth, such as for suctioning, performing spirometry, incentive spirometry, peak flow, and other types of respiratory care and oral care;

the ability for the patient to speak with less hindrance during treatment; the ability to drink through a straw during treatment; the reduced probability of aspiration; and the accommodation of a nasogastric intubation tube for feeding and medicinal administration.

Along this medical gas tubing is at least one swivel element that is able to rotate freely to release twisting and tension on the medical gas tubing. Said swivel element can be located in the vicinity of the dampening disperser.

Figure 11A:
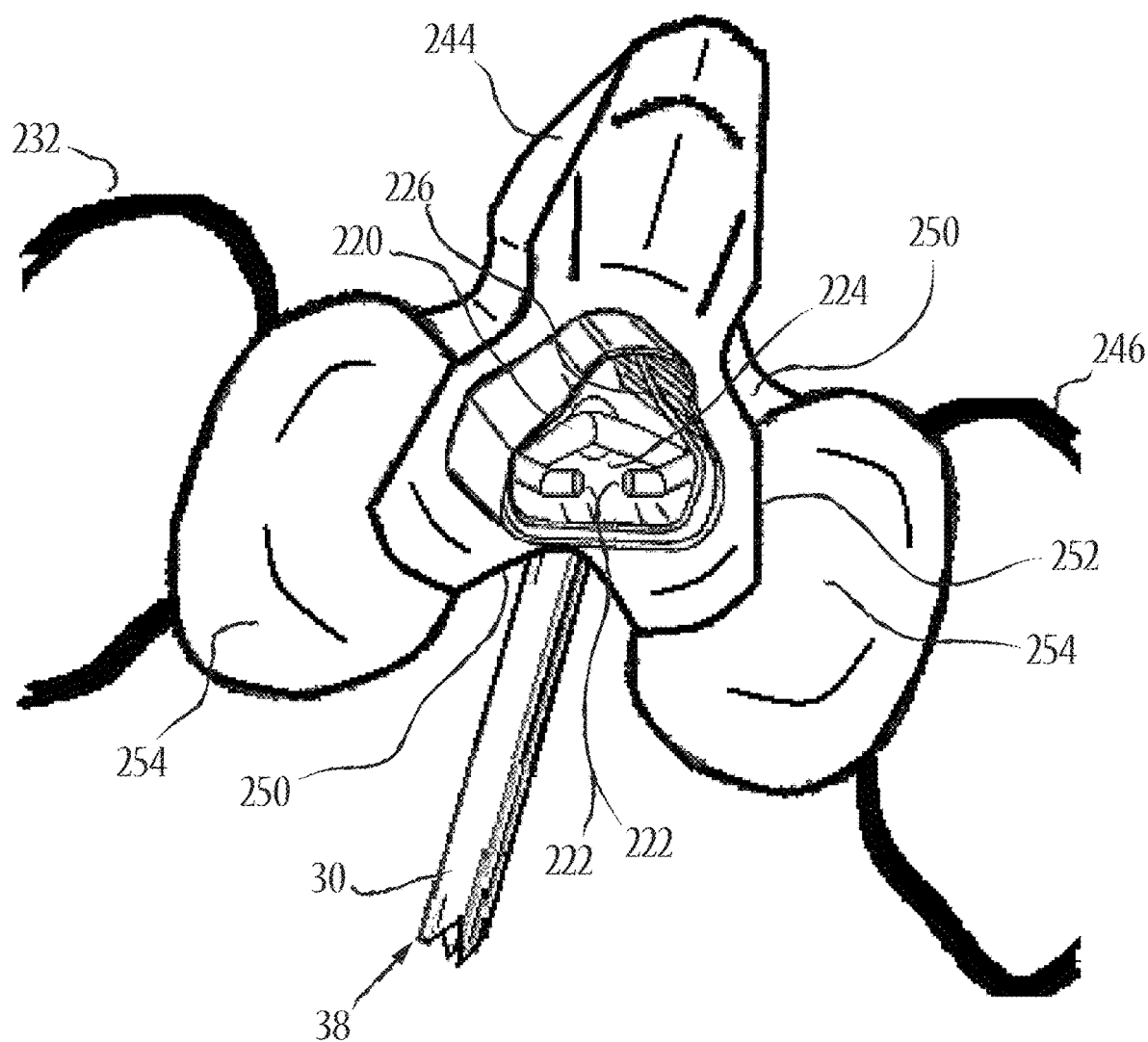
FIG. 11A is a detailed inner view of the dampening disperser and partial face mask housing of one of the third preferred embodiments of the universal medical gas delivery system. The disperser includes two gas outlet nozzles that release medical gas in somewhat counterposing directions to reduce gas velocity and to generate vortexing and mixing of gas with ambient air through gaps in the partial face mask housing. Elastic straps comprise the patient head interface in this figure. Cushioning elements and face mask rim are also shown.

In a third preferred embodiment FIG. 11A, the medical gas delivery system 10 includes at least one dampening disperser 220 configured to be supported in a position in front of a patient's face. The dampening disperser 220 includes at least some concave walls 226 of an at least a partial face mask housing 244, and at least two gas outlets nozzles 222 that release medical gas within the interior region 224 formed by the concave interior walls 226 of the dampening disperser. The nozzles are in at least partially counterposing directions to disperse and reduce the velocity/impact of the gas flow 230 directed at the patient and coming from the at least one supply tubing 30 attached to an at least one medical gas source outlet 22 or 82. A turbulent plume of gases is generated that mix with ambient air in the space 228 in the vicinity of the patient's nose and mouth, such as between the upper lip and the base of the nose. In this manner both nose breathing and mouth breathing are allowed of these gases the clearance of exhaled breath away from the patient is aided so as to diminish the rebreathing of exhaled air. Said dampening disperser can be attached to a variety of different supports 232 in communication with the patient's head to position the dampening disperser in the vicinity of the patient's nose and mouth.

Figure 11B:
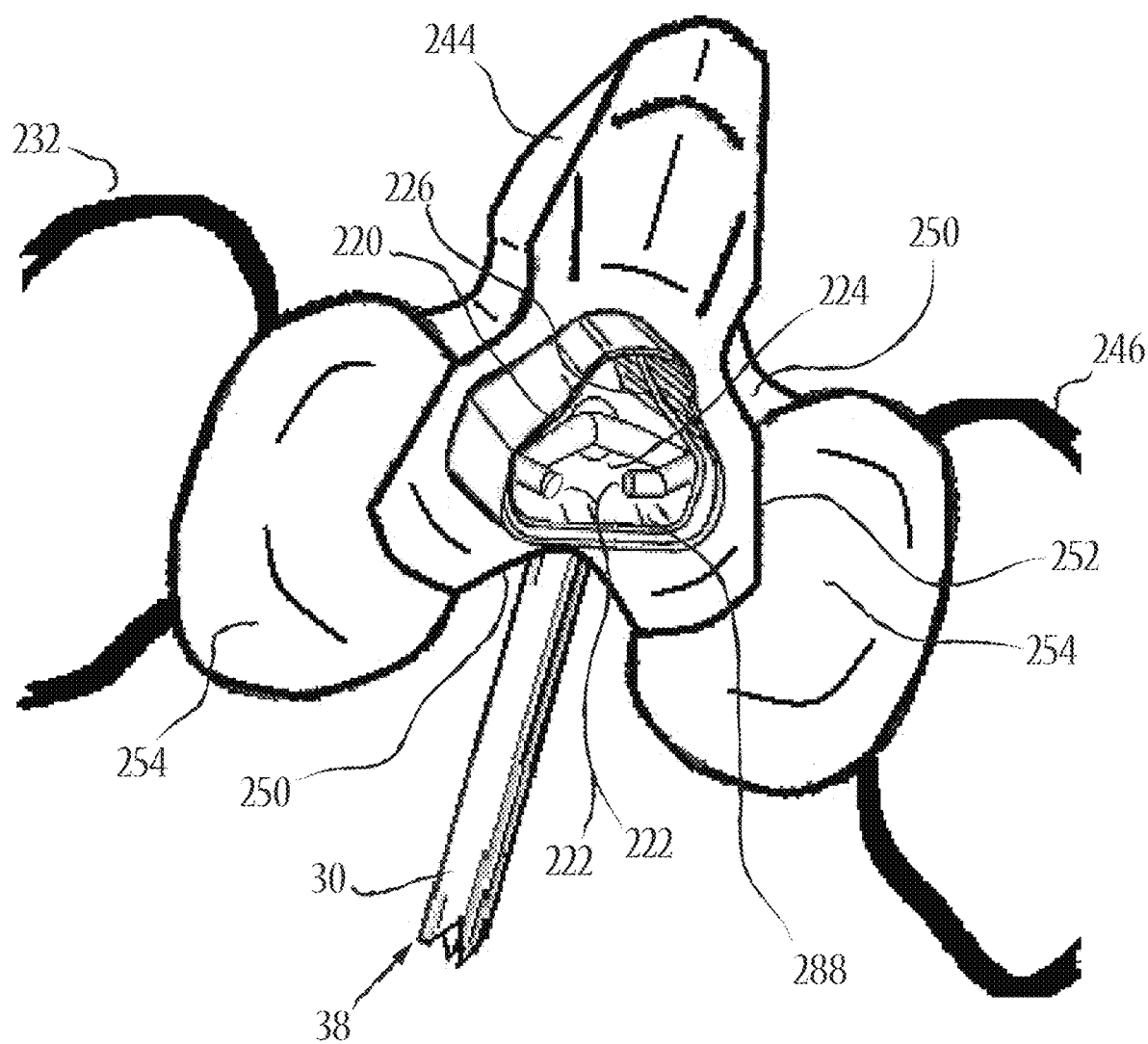
FIG. 11B is a detailed inner view of a partial face mask housing with an alternate dampening disperser, which includes two gas outlet nozzles that release medical gas in somewhat counterposing directions, in which one of the two gas outlet nozzles also releases medical gas in a direction at least partially toward an at least one baffling-surface associated with the concave walls of an at least a partial face mask housing to impact this baffling-surface, to reduce gas velocity and to generate vortexing and mixing of gas with ambient air through gaps in the partial face mask housing.

FIG. 11B shows a similar third preferred embodiment with two gas outlets nozzles 222, but with one gas outlet nozzle 222 (shown on the left) positioned or angled differently so as to release at least some medical gas in a direction at least partially toward said at least some concave walls 226 to at least partially impact with said at least one baffling-surface 288 associated with said at least some concave walls 226. Therefore, the medical gas delivery system 10 includes at least one dampening disperser 220; configured to be supported in a position in front of a patient's face, said dampening disperser 220 including at least some concave walls 226 of an at least a partial face mask housing 244, and at least one gas outlet nozzle 222 that releases medical gas in a direction at least partially toward an at least one baffling-surface 288 associated with said at least some concave walls 226, said at least one gas outlet nozzle 222 serving to disperse and reduce a velocity of a gas flow 230 coming from at least one medical gas supply tubing 30 attached to an at least one medical gas source outlet 22 or 82, while generating at least one plume of gases that mix with air in a space 228 in a vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air. A second gas outlet nozzle 222 may be optional. In this figure, a second gas outlet nozzle 222 (shown on the right) does not point at the least one baffling-surface 288 associated with said at least some concave walls 226, but still releases at least some medical gas in at least partially counterposing directions with the first gas outlet nozzle.

As can be seen from FIGS. 11A and 11B, it can be desirable for at least one gas outlet nozzle 222 to be positionable, bendable or rotatable, so as to adjust the angle of the delivery of said medical gas. A positionable gas outlet nozzle would allow the user to adjust the angle of incidence of gas flow impacting with a baffling-surface 288 associated with said at least some concave walls 226, and/or the angle of incidence of counterposing gas flows, and/or even the angle of incidence with an alternative or secondary baffle. It can also be desirable for at least one gas outlet nozzle 222 to be flow-alterable to adjust the delivery of said medical gas flow, and thus, the amount of impact. This can be achieved by bending or changing diameters.

Figure 11C:
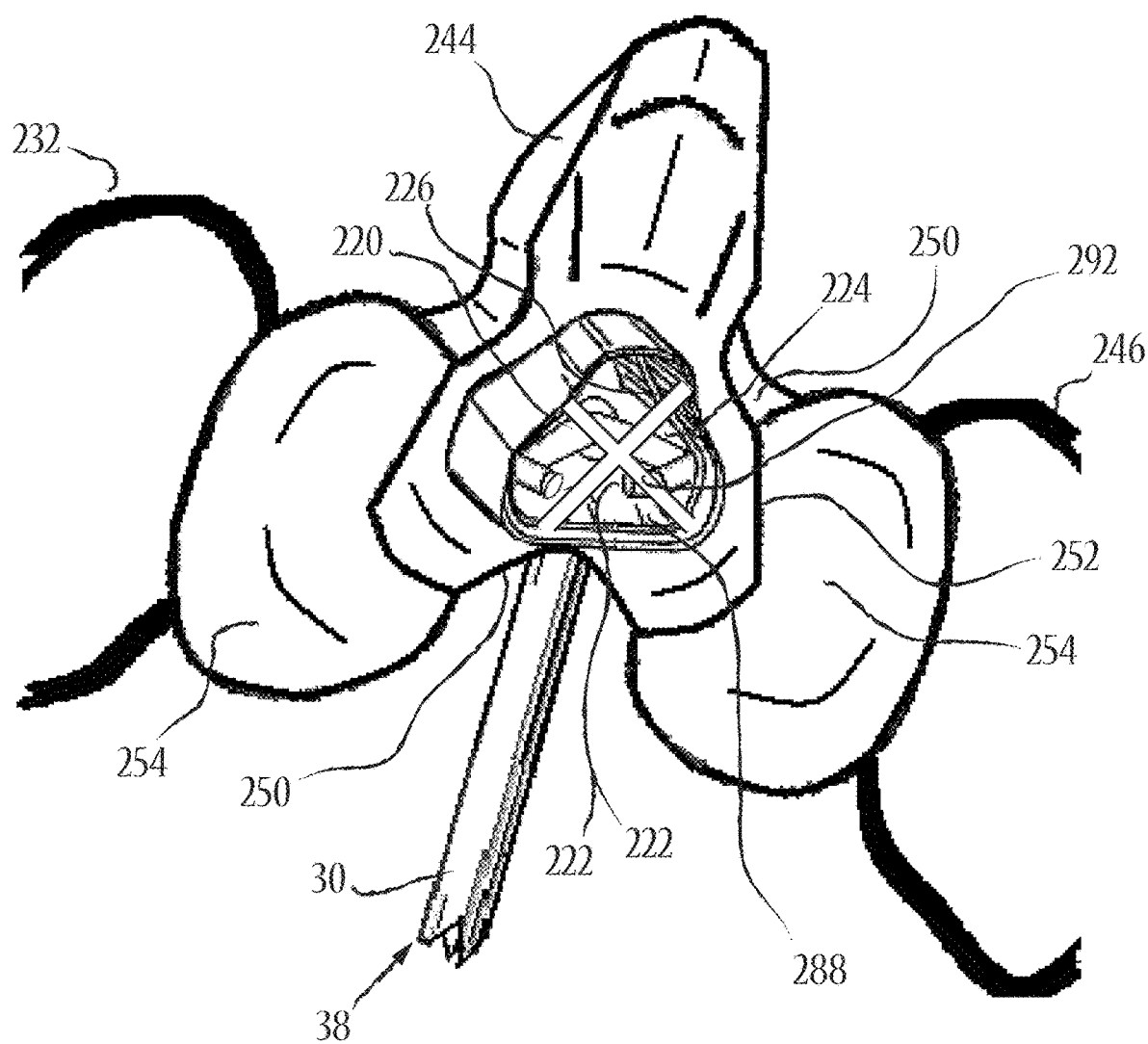
FIG. 11C shows a third preferred embodiment similar to FIGS. 11A and 11B, but with an X-shaped baffle 292 attached to and going across at least some concave walls of the at least a partial face mask housing.

FIG. 11C shows a third preferred embodiment similar to FIGS. 11A and 11B, but with an X-shaped baffle 292 attached to and going across said at least some concave walls 226 of an at least a partial face mask housing 244. This baffle 292 is at least partially in a path of gas flow 230 to further disperse and reduce a velocity of this gas flow. Baffle 292 is shown as an X-shaped baffle, but other shapes can be used so that this example of a baffle is not meant to be limiting.

Figure 12:
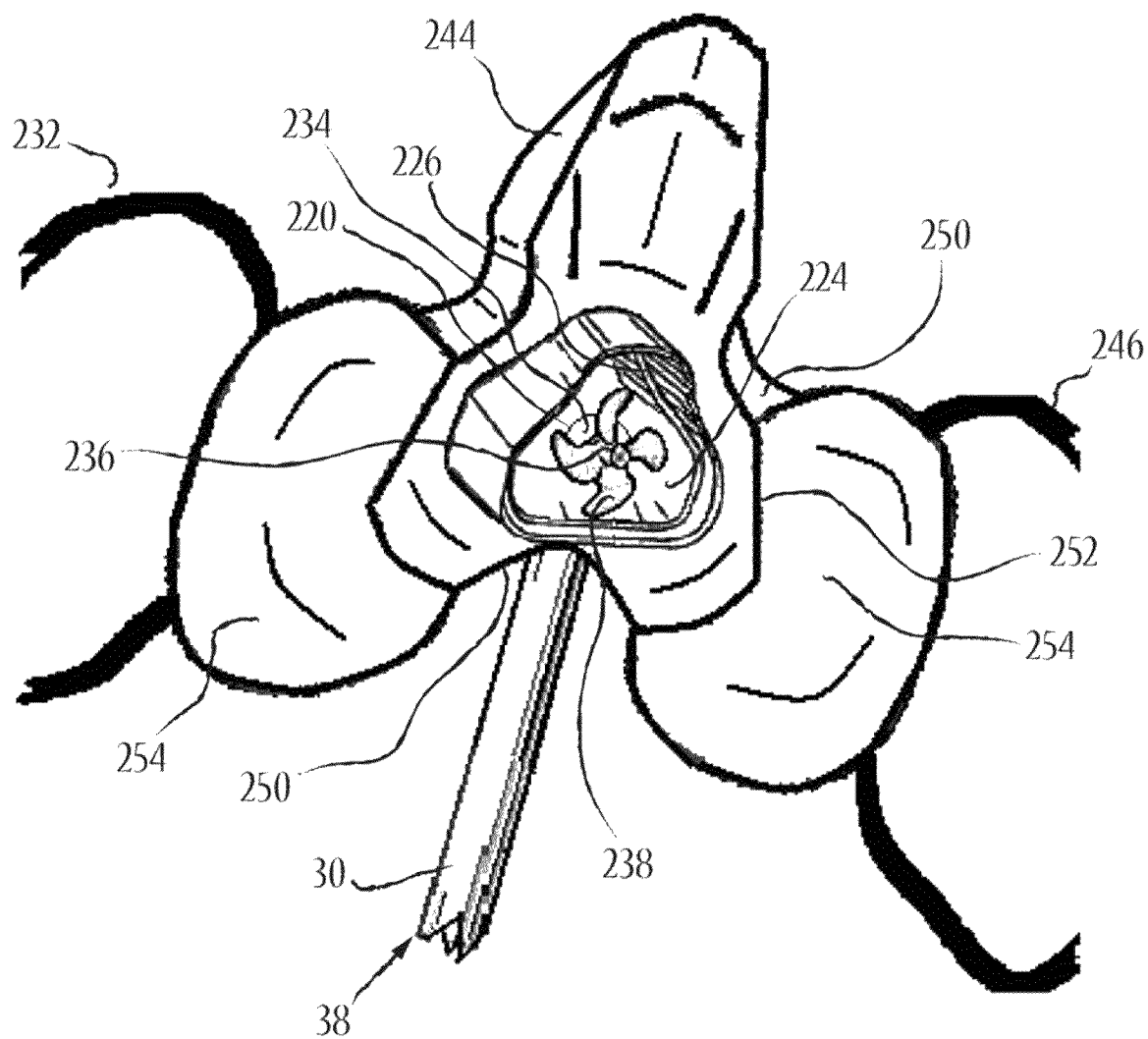
FIG. 12 is a detailed inner view of a partial face mask housing with an alternate dampening disperser, which includes a gas nozzle and a non-stationary baffle (impeller) that can reduce gas velocity and generate vortexing and mixing of gas with ambient air, as well as, to indicate air flow when in use.

In another third preferred embodiment FIG. 12, the least one dampening disperser 220 is configured to be supported in a position in front of a patient's face. The dampening disperser 220 includes at least some concave walls 226 of an at least a partial face mask housing 244, and at least one gas outlet nozzle 234 that releases medical gas within the interior region 224 formed by the concave interior walls 226 of the dampening disperser. At least one non-stationary baffle 236 is in the path of this gas flow to disperse and create drag. In this manner, the velocity/impact of the gas flow 230 is directed at the patient and is coming from the at least one supply tubing 30 attached to an at least one medical gas source outlet 22 or 82. This non-stationary baffle can also create cyclonic motion and vortices. A turbulent plume of gases is generated that mixes with ambient air in the space 228 in the vicinity of the patient's nose and mouth, such as between the upper lip and the base of the nose. Again, in this manner, both nose breathing and mouth breathing of these gases is allowed and the clearance of exhaled breath away from the patient is aided so as to diminish the rebreathing of exhaled air. Movement of said non-stationary baffle 236 may be visualized to indicate that the patient is receiving gas flow. The at least one gas outlet nozzle 234, and the at least one non-stationary baffle 236, may each be preferably positionable to adjust the delivery of the medical gas. The dampening disperser can be attached to a variety of different supports 232 in communication with the patient's head to position the dampening disperser in the vicinity of the patient's nose and mouth. Non-stationary baffles 236 can be chosen from a class of baffles selected from a type of non-stationary baffles including, but not limited to, flexible flaps, sails, parachutes, wings and blades and rotating blades 238, such as that of a fan, impeller, and windmill. In some embodiments, ball valves, butterfly valves, or other throttle valves and related structures can be used with, or serve as, non-stationary baffles. The at least one non-stationary baffle 236 is preferably replaceable with a different non-stationary baffle from this class of non-stationary baffles to adjust the delivery of the medical gas.

Figure 13:
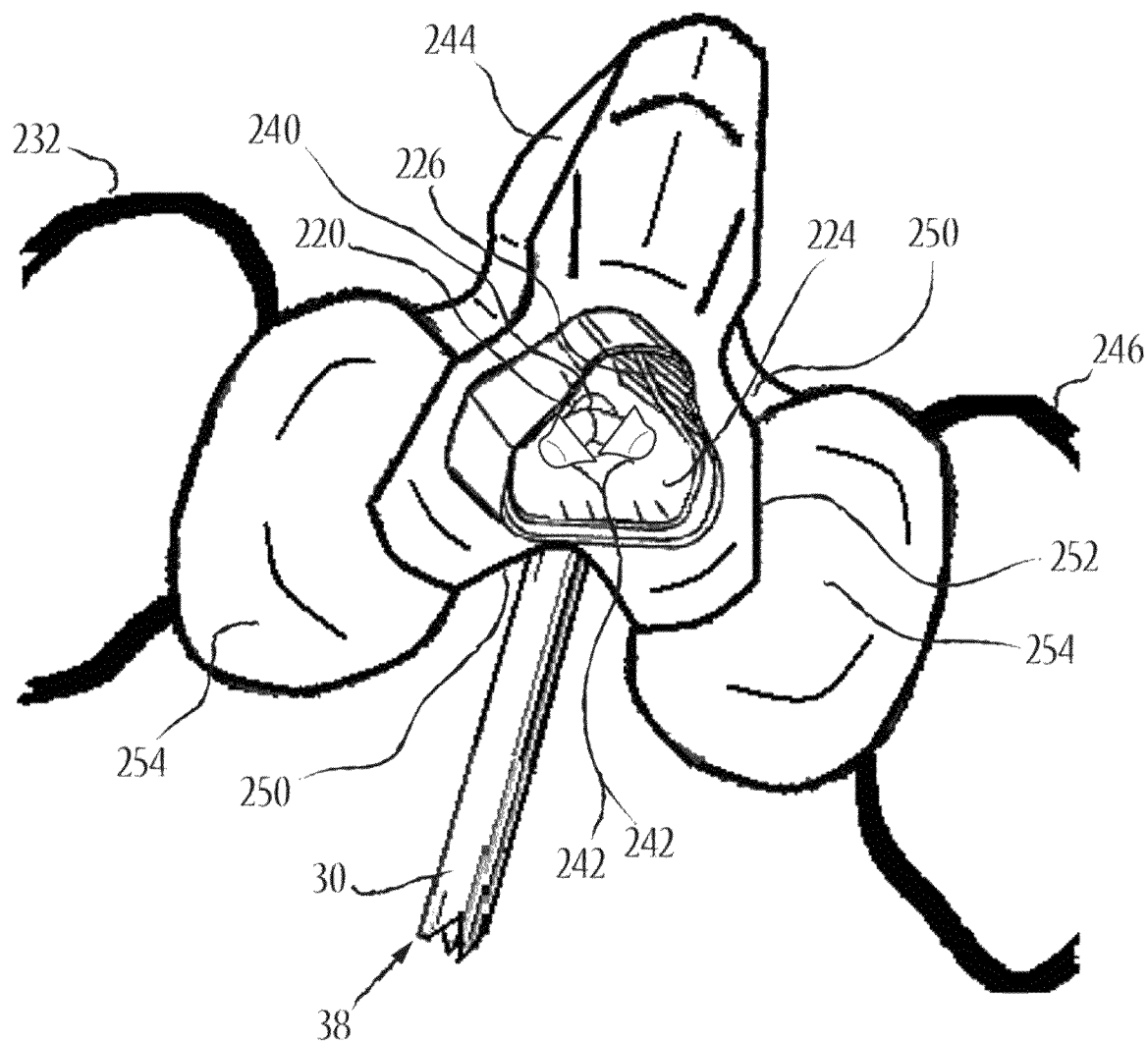
FIG. 13 is a detailed inner view of a partial face mask housing with an alternate dampening disperser, which includes two gas outlet nozzles positioned with two stationary (mushroom-like) baffles in its air flow trajectory, to reduce gas velocity and generate vortexing and mixing of gas with ambient air.

In another third preferred embodiment FIG. 13, the least one dampening disperser 220 is configured to be supported in a position in front of a patient's face. The dampening disperser 220 includes at least some concave walls 226 of an at least a partial face mask housing 244, and at least one gas outlet nozzle 240 that releases medical gas within the interior region 224 formed by the concave interior walls 226 of the dampening disperser. At least two baffles 242 are in the path of this gas flow to disperse and reduce the velocity/ impact of the gas flow 230 directed at the patient and coming from the at least one supply tubing 30 attached to an at least one medical gas source outlet 22 or 82. A turbulent plume of gases is generated that mix with ambient air in the space 228 in the vicinity of the patient's nose and mouth, such as between the upper lip and the base of the nose. In this manner, both nose breathing and mouth breathing of these gases is allowed and the clearance of exhaled breath away from the patient is aided so as to diminish the rebreathing of exhaled air. The at least one gas outlet nozzle 240, and the at least two baffles 242, may each be preferably positionable to adjust the delivery of the medical gas. The at least two baffles 242 are also preferably replaceable with different baffles, baffles having different size and or shape, to adjust the delivery of said medical gas. The dampening disperser can be attached to a variety of different supports 232 in communication with the patient's head to position the dampening disperser in the vicinity of the patient's nose and mouth.

Figure 17A:
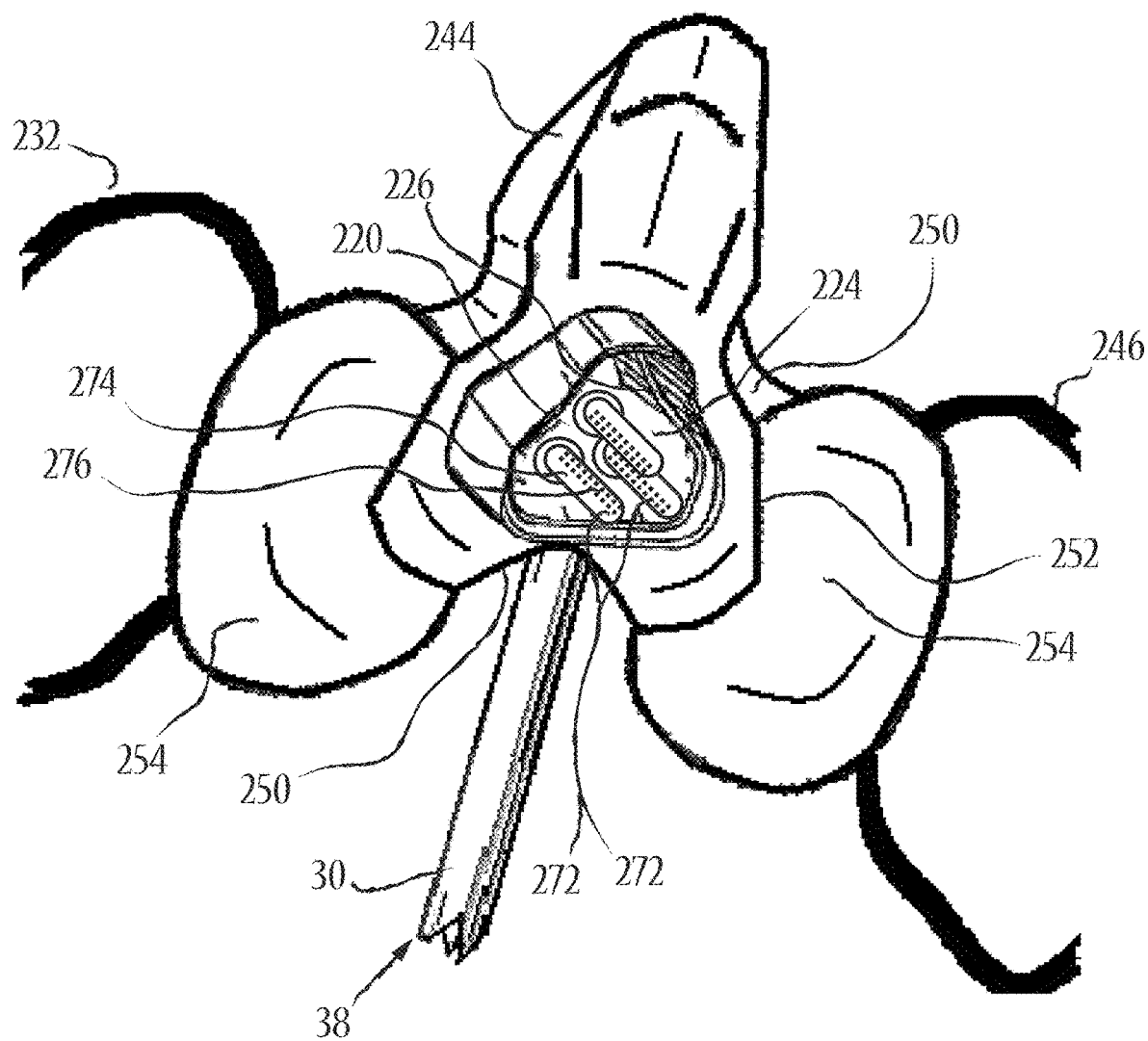
FIG. 17A is a detailed inner view of a partial face mask housing with an alternate dampening disperser, which includes at least one gas multi-outlet nozzle including an at least a partial tubular structure with a plurality of small/micro gas outlets to disperse and reduce a velocity of a gas flow and to generate vortexing and mixing of gas. This figure is shown with three gas multi-outlet nozzles, each having a straight tubular structure.
Figure 18A:
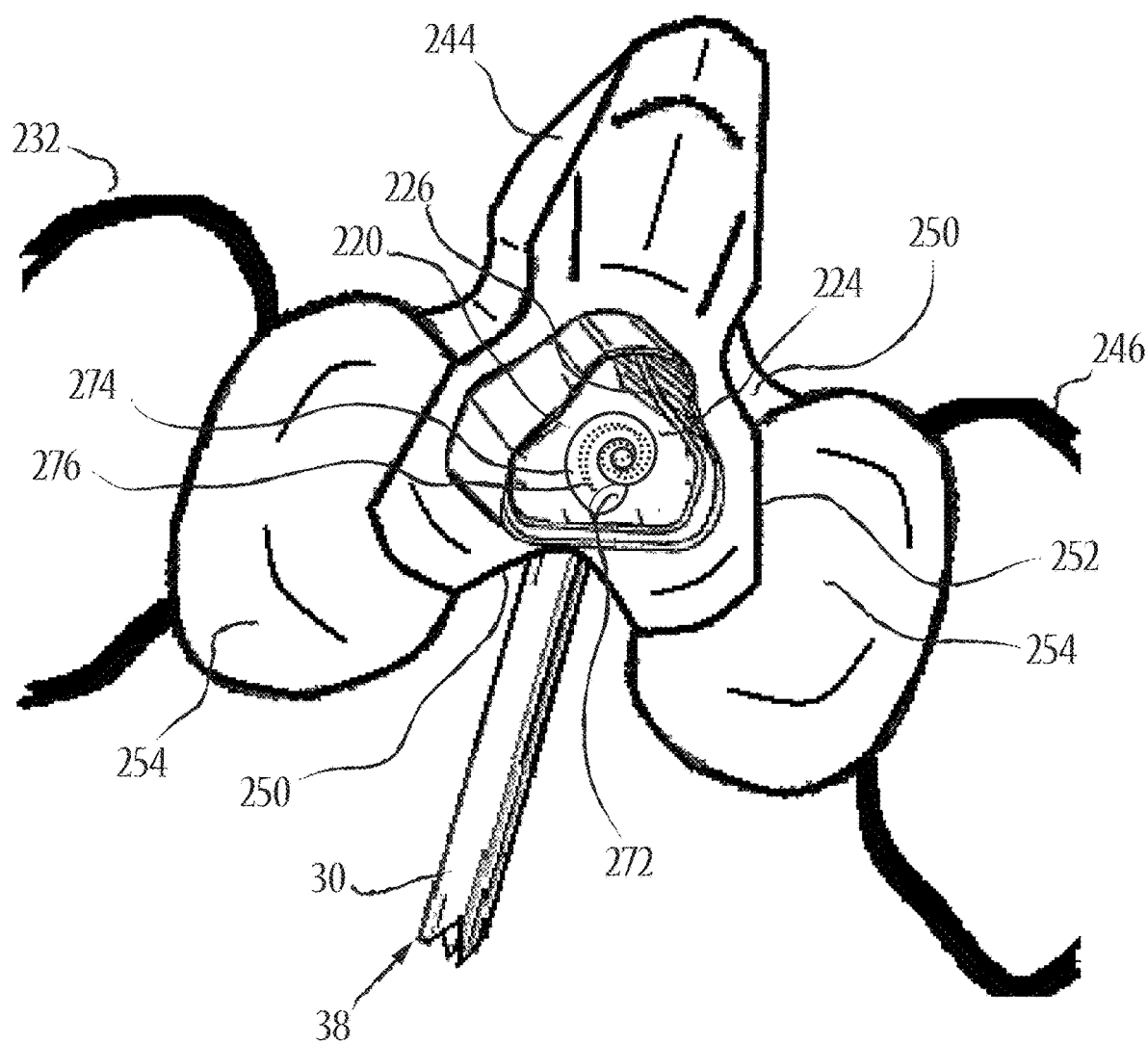
FIG. 18A is a detailed inner view of a partial face mask housing with this alternate dampening disperser, which includes at least one gas multi-outlet nozzle including an at least a partial tubular structure with a plurality of small/micro gas outlets to disperse and reduce a velocity of a gas flow and to generate vortexing and mixing of gas. This figure is shown with one gas multi-outlet nozzle having a curved/spiral tubular structure.

In another third preferred embodiment FIGS. 17A and 18A, the least one dampening disperser 220 is configured to be supported in a position in front of a patient's face. The dampening disperser 220 includes at least some concave walls 226 of an at least a partial face mask housing 244, and at least one gas multi-outlet nozzle 272. The at least one gas multi-outlet nozzle 272 includes an at least a partial tubular structure 274 with a plurality of small/micro gas outlets 276 that release medical gas. The at least one gas multi-outlet nozzle 272 serves to disperse and reduce a velocity of a gas flow 230 coming from at least one medical gas supply tubing 30 attached to an at least one medical gas source outlet 22 or 82, while generating at least one plume of gases that mix with air in a space 228 in the vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air. FIG. 17A shows a dampening disperser 220 with three gas multi-outlet nozzles 272, each having a straight tubular structure 274; while FIG. 18A shows a dampening disperser 220 with one gas multi-outlet nozzle 272 having a curved/spiral tubular structure 274. In FIGS. 17A and 18A, the at least one gas multi-outlet nozzle 272, which includes an at least a partial tubular structure 274 with a plurality of small/micro gas outlets 276, releases at least some medical gas in at least partially counterposing directions. The dampening disperser can be attached to a variety of different supports 232 in communication with the patient's head to position the dampening disperser in the vicinity of the patient's nose and mouth.

Figure 17B:
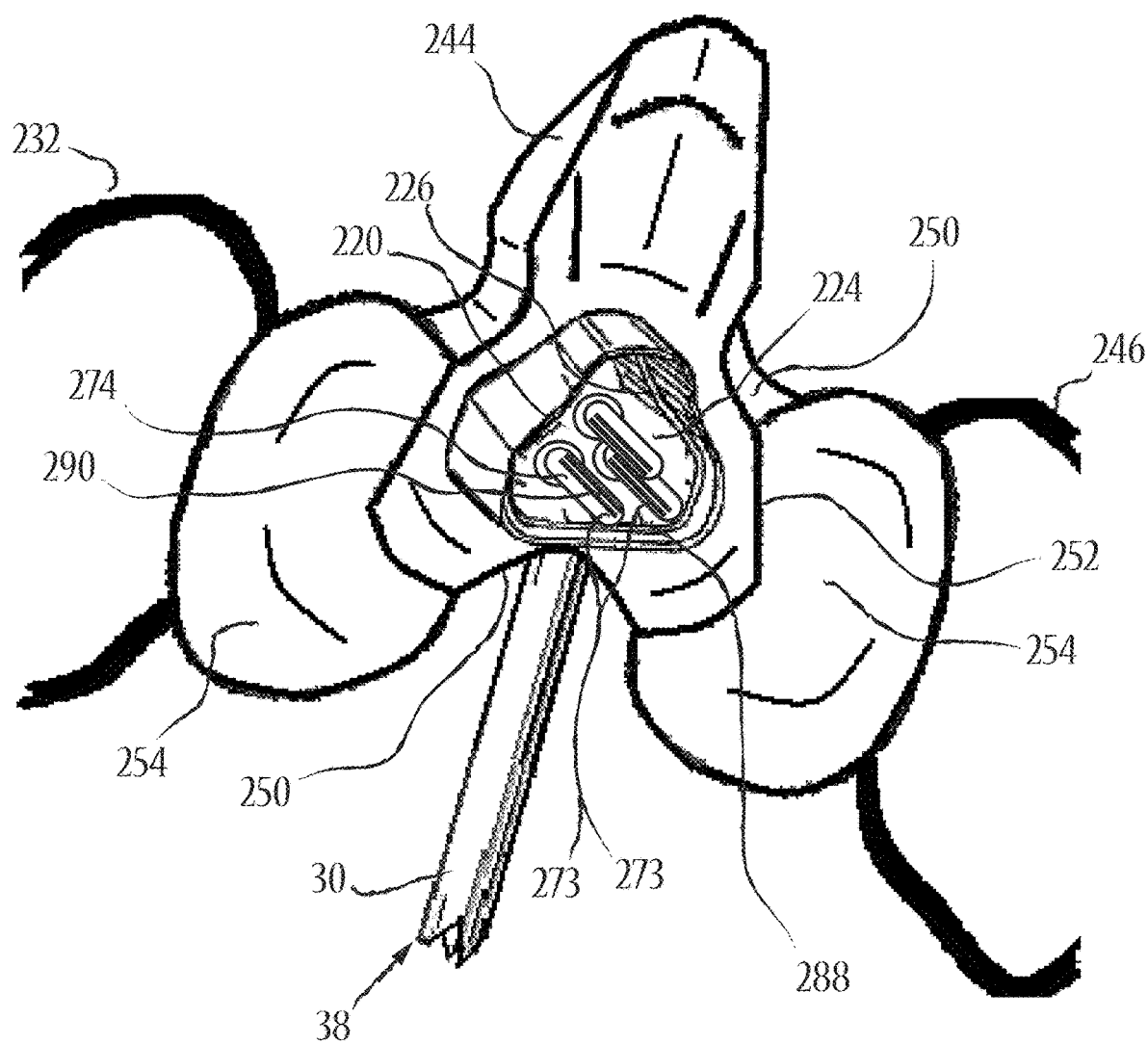
FIG. 17B is similar to FIG. 17A but with some or all of the plurality of small/micro gas outlets replaced with, or merged into, at least one gas vent outlet.
Figure 18B:
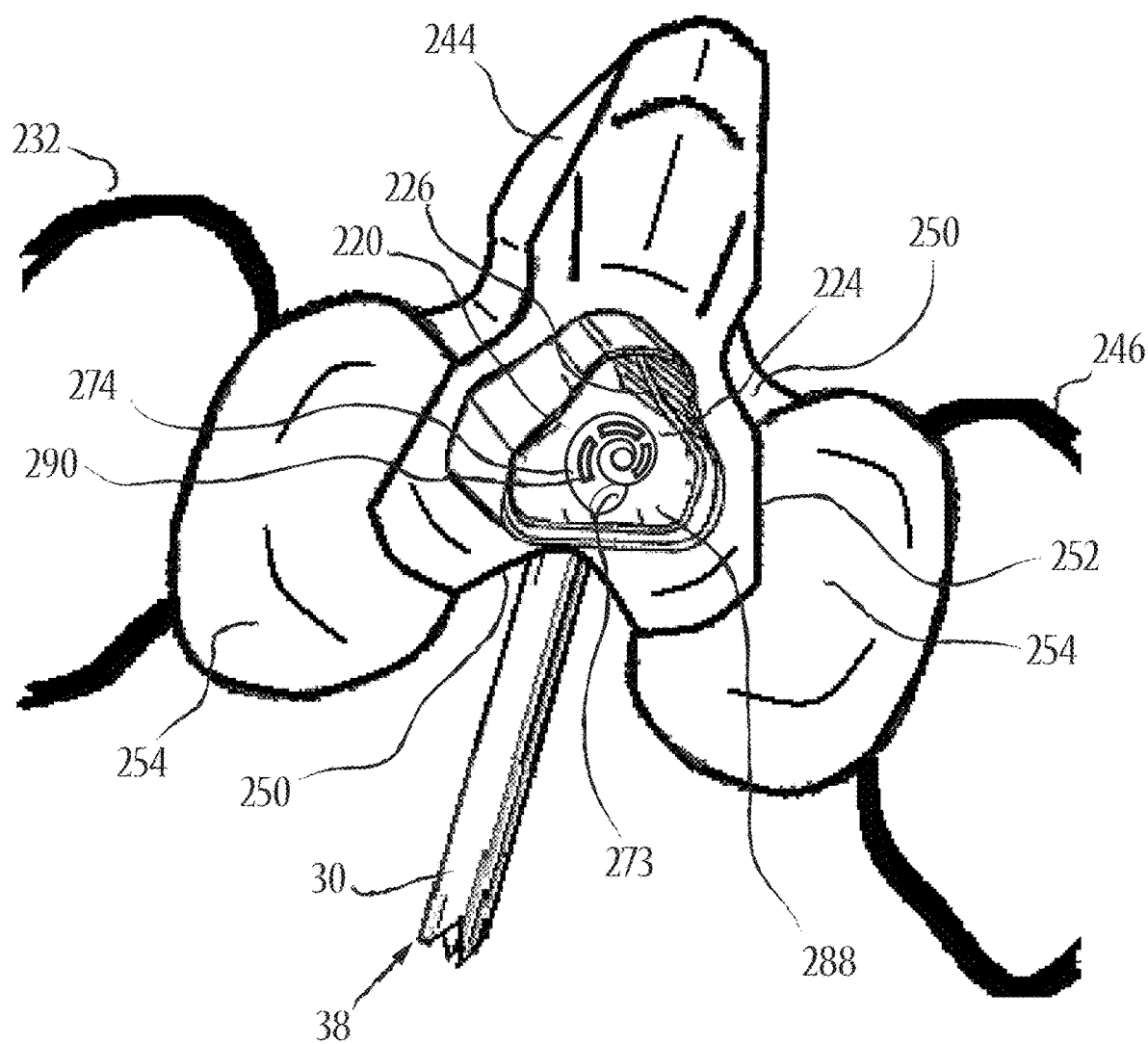
FIG. 18B is similar to FIG. 18A but with some or all of the plurality of small/micro gas outlets replaced with, or merged into, at least one gas vent outlet.

Some or all of the plurality of small/micro gas outlets 276 that release medical gas from the at least one gas multi-outlet nozzle 272 of FIGS. 17A and 18A can be replaced with, or merged into, at least one gas vent outlet 290, as shown in FIGS. 17B and 18B. This at least one gas vent outlet 290 is a larger slit or aperture in or emanating from said at least one gas vented-outlet nozzle 273. FIG. 17B shows a dampening disperser 220 with three gas vented-outlet nozzles 273, each having a straight tubular structure 274; while FIG. 18B shows a dampening disperser 220 with one gas vented-outlet nozzle 273 having a curved/spiral tubular structure 274.

The at least one gas vent outlet 290 can release at least some medical gas in a direction at least partially toward said at least some concave walls 226 to at least partially impact with a baffling-surface 288 associated with said at least some concave walls 226, and/or release at least some medical gas to at least partially impact with at least one baffle 292, and/or release at least some medical gas in at least partially counterposing directions to a second gas vent outlet.

FIGS. 17B and 18B therefore show a medical gas delivery system that includes at least one dampening disperser 220; configured to be supported in a position in front of a patient's face, said dampening disperser 220 including at least some concave walls 226 of an at least a partial face mask housing 244, and at least one gas vented-outlet nozzle 273, said at least one gas vented-outlet nozzle 273 including an at least a partial tubular structure 274 with at least one gas vent outlet 290 that releases medical gas, said at least one gas vented-outlet nozzle 273 serving to disperse and reduce a velocity of a gas flow 230 coming from at least one medical gas supply tubing 30 attached to an at least one medical gas source outlet 22 or 82, while generating at least one plume of gases that mix with air in a space 228 in a vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air.

Figure 17C:
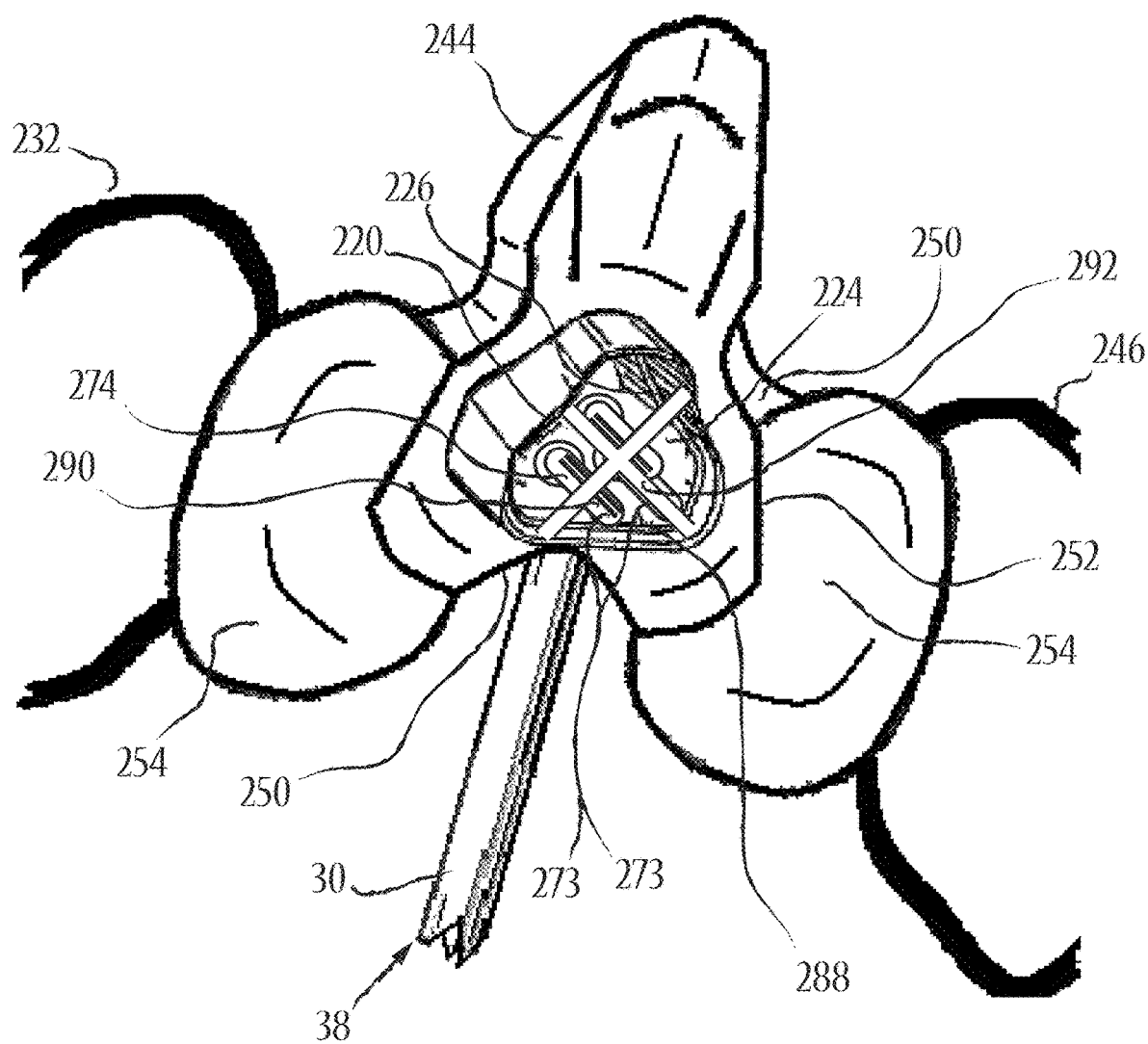
FIG. 17C show a third preferred embodiment similar to FIGS. 17A and 17B, but with an X-shaped baffle attached to and going across at least some concave walls of the at least a partial face mask housing.
Figure 18C:
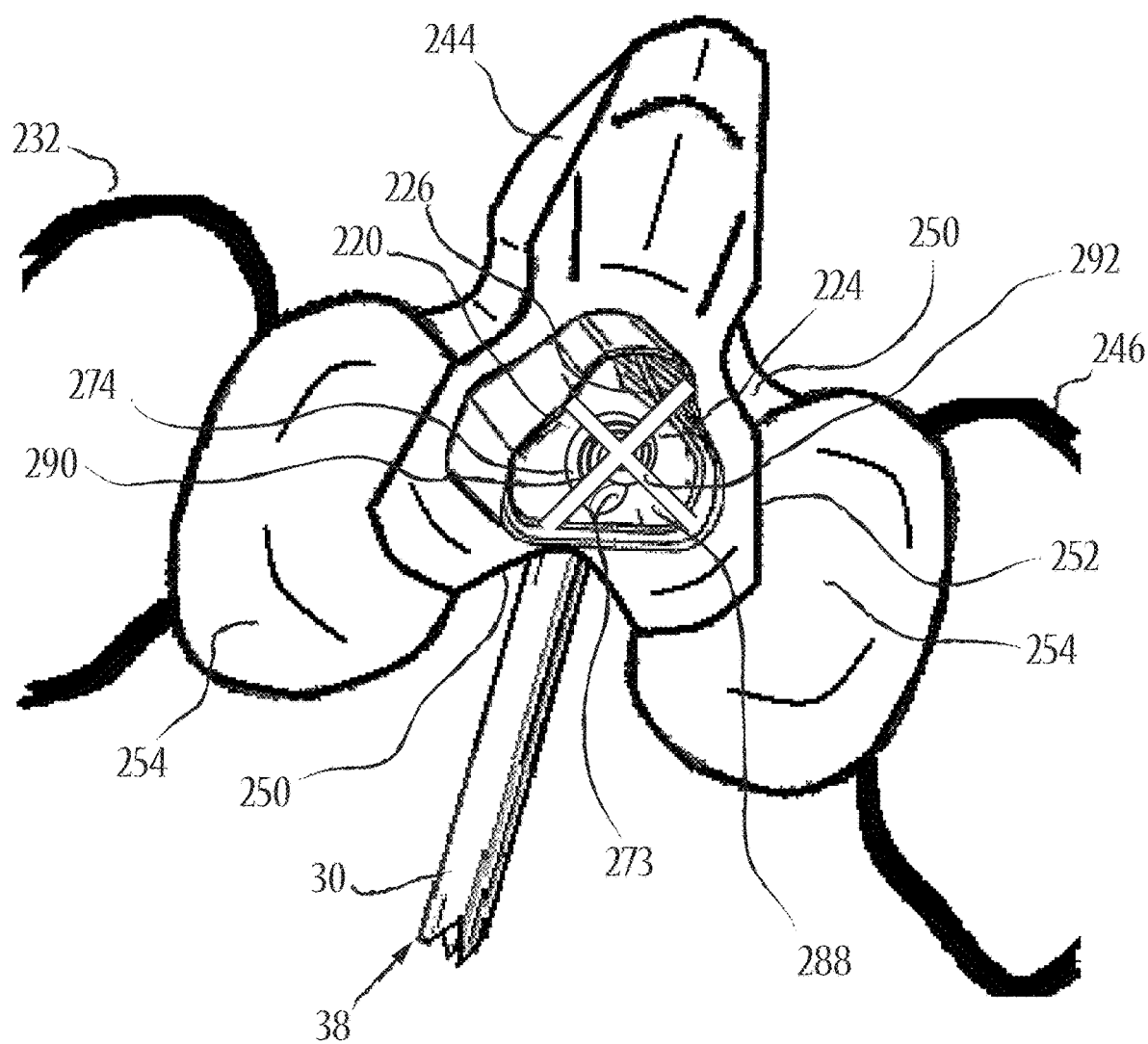
FIG. 18C show a third preferred embodiment similar to FIGS. 18A and 18B, but with an X-shaped baffle attached to and going across at least some concave walls of the at least a partial face mask housing.

FIGS. 17C and 18C show a third preferred embodiment similar to FIGS. 17A-18B, but with an X-shaped baffle 292 attached to and going across said at least some concave walls 226 of an at least a partial face mask housing 244. This baffle 292 is at least partially in a path of gas flow 230 to further disperse and reduce a velocity of this gas flow. Baffle 292 is shown as an X-shaped baffle, but other shapes can be used so that this example of a baffle is not meant to be limiting.

Figure 19A:
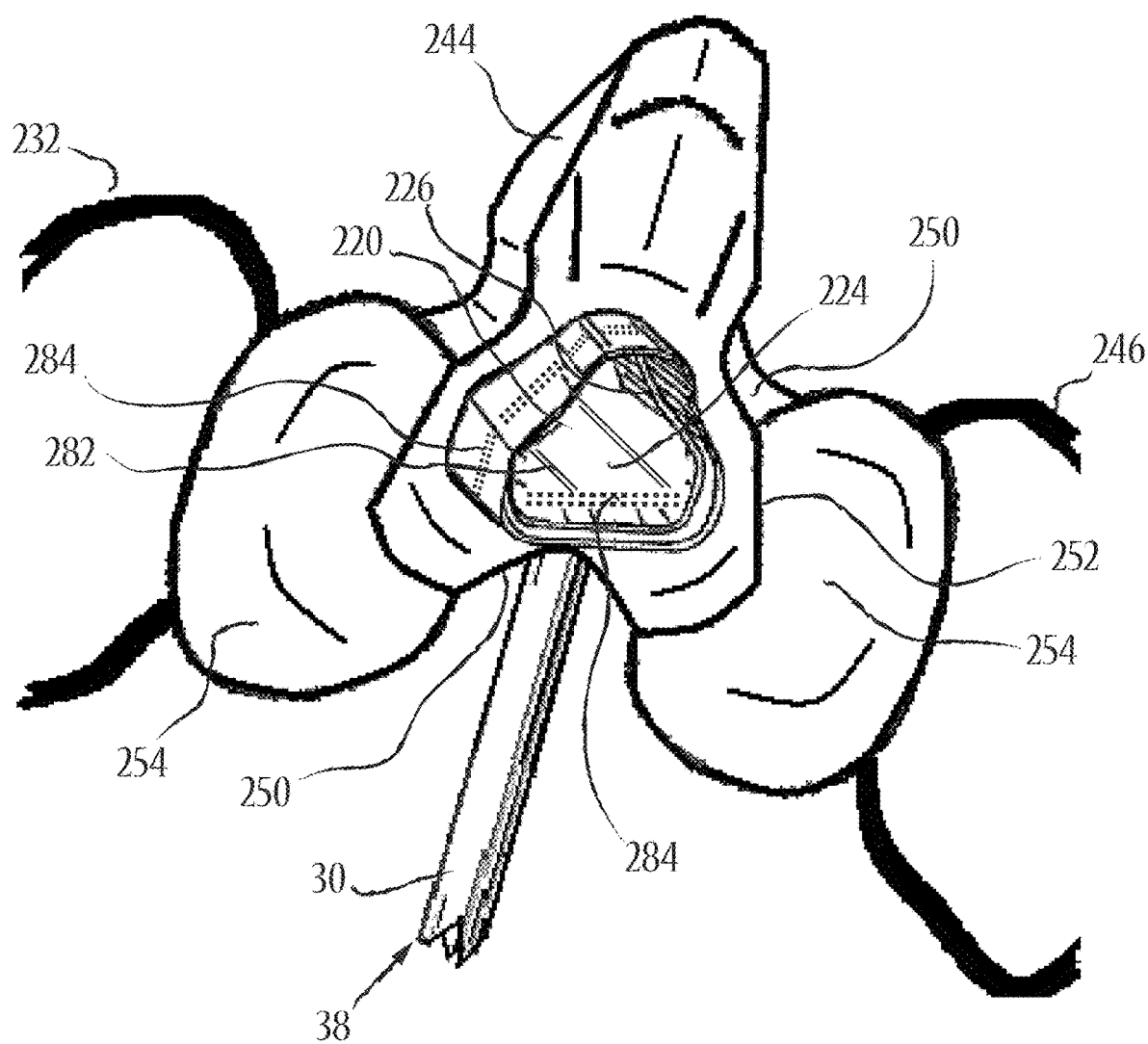
FIG. 19A is a detailed inner view of a partial face mask housing with an alternate dampening disperser, which includes channels/space within at least some concave walls of the partial face mask housing and adapted for a medical gas to pass. These at least some concave walls further include a plurality of small/micro gas outlets to disperse, refocus and reduce a velocity of a gas flow and to generate vortexing and mixing of gas.

In another third preferred embodiment FIG. 19A, the least one dampening disperser 220 is configured to be supported in a position in front of a patient's face. The dampening disperser 220 includes at least some concave walls 226 of an at least a partial face mask housing 244. The at least some concave walls 226 of an at least a partial face mask housing 244 includes channels/space 282 within, which are adapted for a medical gas to pass. These at least some concave walls 226 of an at least a partial face mask housing 244 further include a plurality of small/micro gas outlets 284 on at least some portion of its surface that release medical gas in an interior region 224. The at least some concave walls 226 of an at least a partial face mask housing 244, which includes channels/space 282 within and a plurality of small/micro gas outlets 284, serve to disperse, refocus and reduce a velocity of a gas flow 230 coming from at least one medical gas supply tubing 30 attached to an at least one medical gas source outlet 22 or 82, while generating at least one plume of gases that mix with air in a space 228 in the vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air. The at least some concave walls 226 of an at least a partial face mask housing 244 with a plurality of small/micro gas outlets 284 release at least some medical gas in at least partially counterposing directions. The dampening disperser can be attached to a variety of different supports 232 in communication with the patient's head to position the dampening disperser in the vicinity of the patient's nose and mouth. In some embodiments, the at least some concave walls 226 preferably form an at least a partial prism-like shape.

Figure 19B:
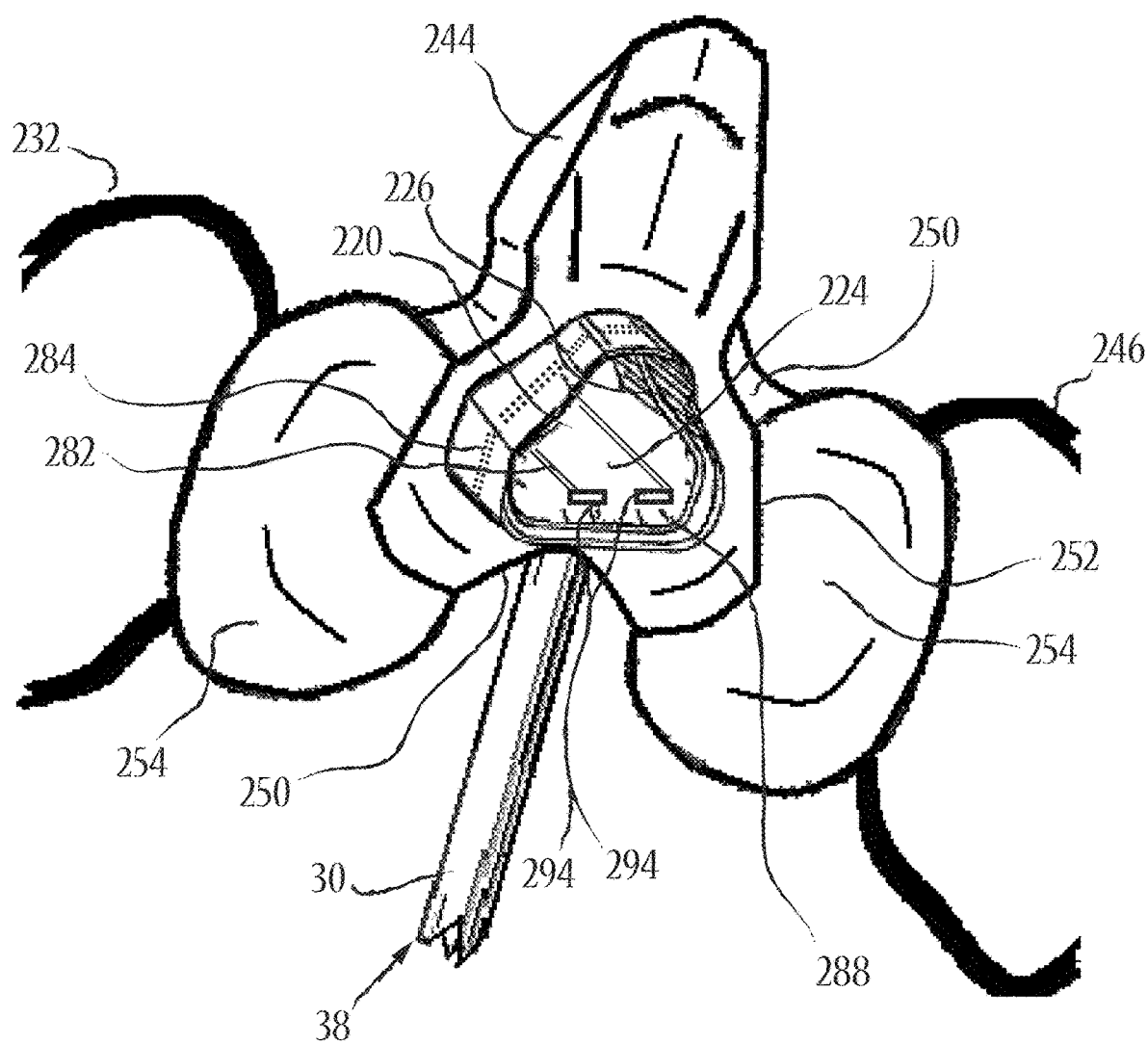
FIG. 19B is similar to FIG. 19A but with some or all of the plurality of small/micro gas outlets replaced with, or merged into, at least one gas vent outlet emanating from at least some portion of the surface of at least some concave walls of the at least a partial face mask housing.

Some or all of the plurality of small/micro gas outlets 284 of FIG. 19A can be replaced with, or merged into, at least one gas vent outlet 294, as shown in FIG. 19B. This at least one gas vent outlet 294 is a larger slit or aperture in or emanating from at least some portion of the surface of at least some concave walls 226 of an at least a partial face mask housing 244. The at least one gas vent outlet 294 can release at least some medical gas in a direction at least partially toward said at least some concave walls 226 to at least partially impact with a baffling-surface 288 associated with said at least some concave walls 226, and/or release at least some medical gas to at least partially impact with at least one baffle 292, and/or release at least some medical gas in at least partially counterposing directions to a second gas vent outlet.

FIG. 19B therefore shows a medical gas delivery system that includes at least one dampening disperser 220; configured to be supported in a position in front of a patient's face, said dampening disperser 220 including at least some concave walls 226 of an at least a partial face mask housing 244, said at least some concave walls 226 of said at least a partial face mask housing 244 including at least one channel/space 282 within said at least some concave walls 226 and adapted for a medical gas to pass, said at least some concave walls 226 of said at least a partial face mask housing 244 further including at least one gas vent outlet 294 on at least some portion of a surface that releases said medical gas, said at least some concave walls 226 of said at least a partial face mask housing 244 including said at least one channel/space 282 within and including said at least one gas vent outlet 294 serving to disperse, refocus and reduce a velocity of a gas flow 230 coming from at least one medical gas supply tubing 30 attached to an at least one medical gas source outlet 22 or 82, while generating at least one plume of gases that mix with air in a space 228 in a vicinity of the patient's nose and mouth, chosen from vicinities including, but not limited to, between an upper lip and a base of the patient's nose, to allow for both nose breathing and mouth breathing of said at least one plume of gases and to aid in clearance of exhaled breath away from the patient so as to diminish rebreathing of exhaled air.

Figure 19C:
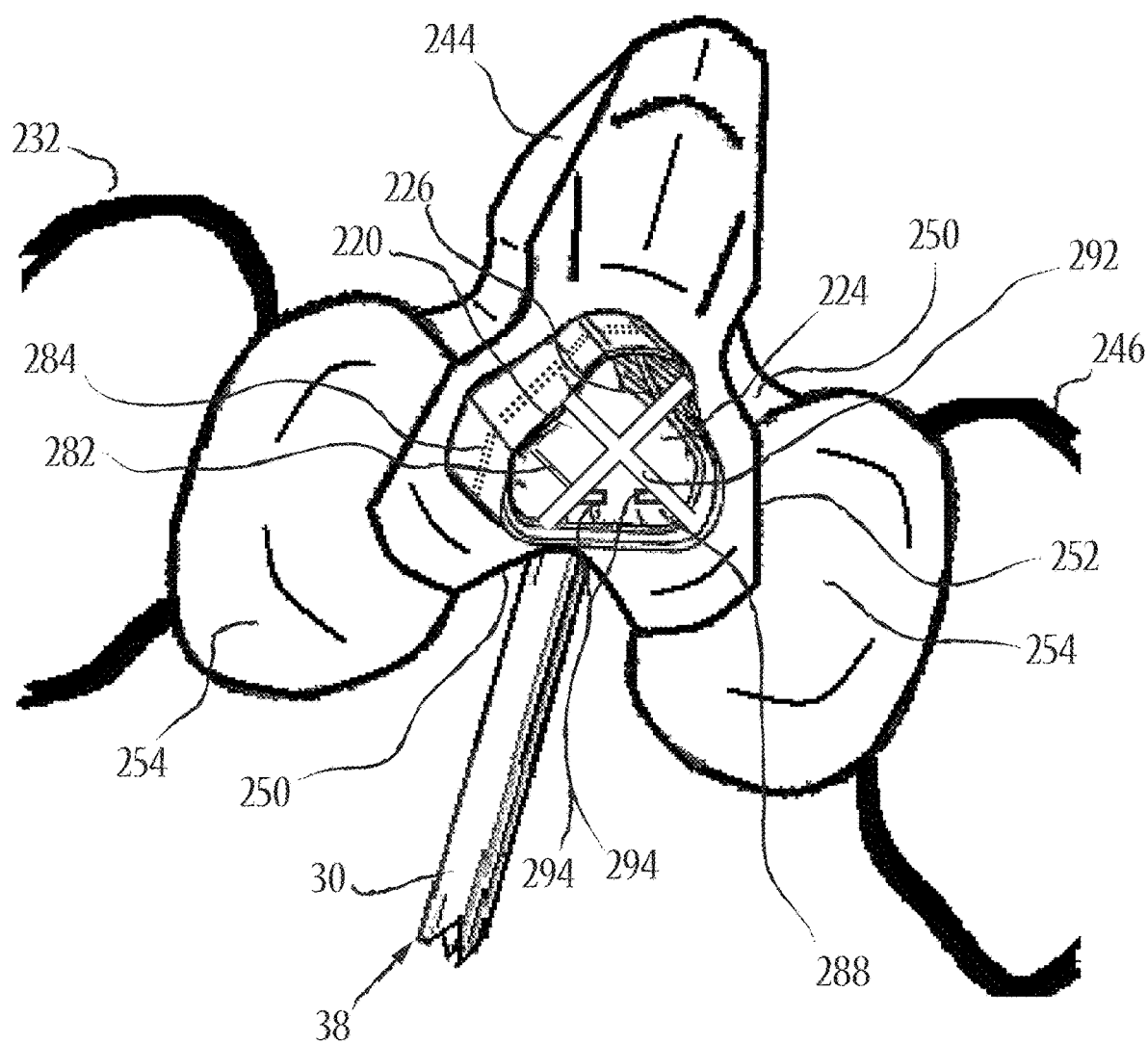
FIG. 19C show a third preferred embodiment similar to FIGS. 19A and 19B, but with an X-shaped baffle attached to and going across at least some concave walls of the at least a partial face mask housing.

FIG. 19C shows a third preferred embodiment similar to FIGS. 19A and 19B, but with an X-shaped baffle 292 attached to and going across said at least some concave walls 226 of an at least a partial face mask housing 244. This baffle 292 is at least partially in a path of gas flow 230 to further disperse and reduce a velocity of this gas flow. Baffle 292 is shown as an X-shaped baffle, but other shapes can be used so that this example of a baffle is not meant to be limiting.

Figure 14:
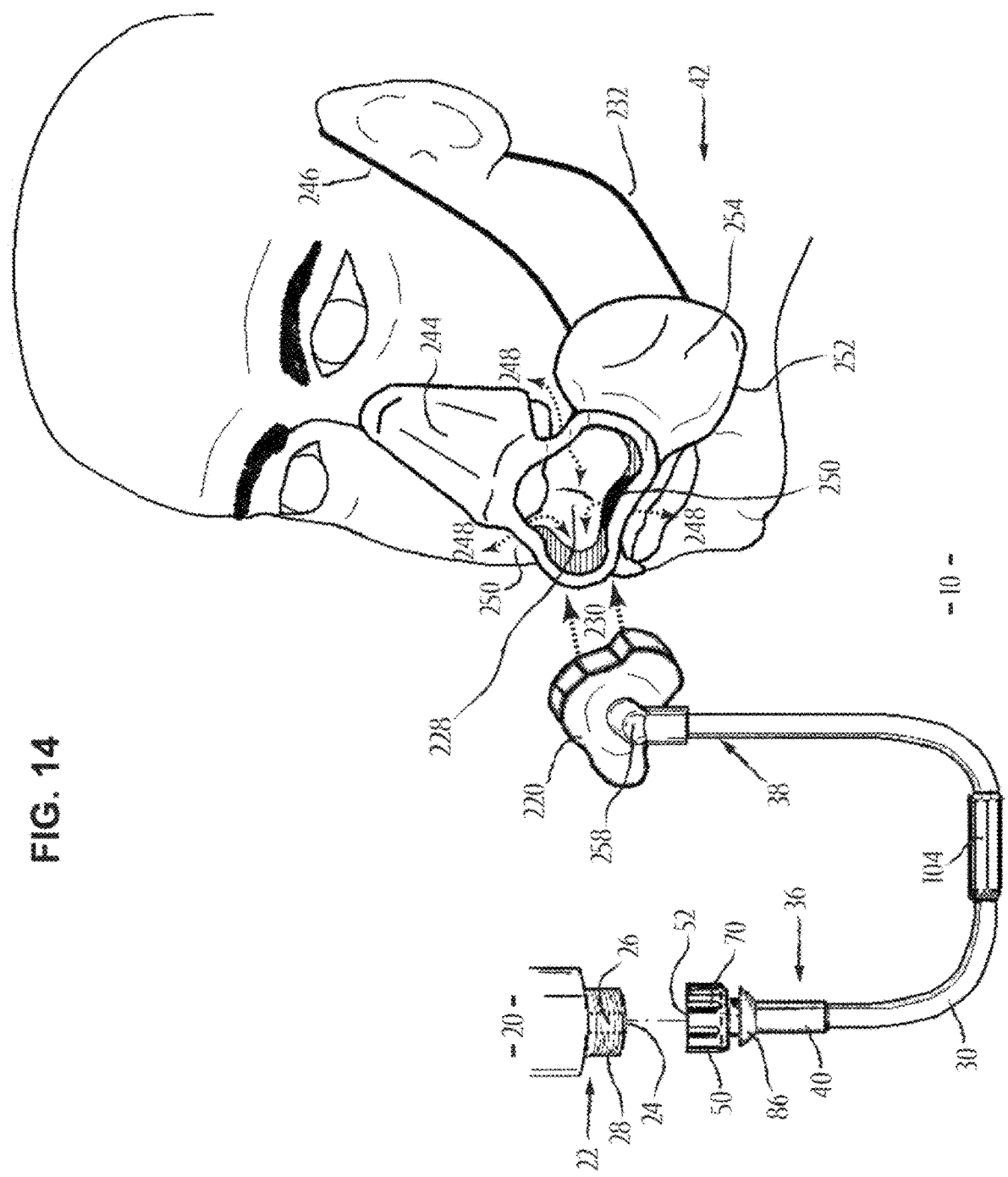
FIG. 14 is a side view of the universal medical gas delivery system of FIG. 1 with its dampening disperser detached from the partial face mask housing so as to show gas flowing from the dampening disperser to the patient, as well as, ambient air mixing in, and exhaled breath mixing out, of the space in the vicinity of the patient's nose and mouth. This figure also shows care giver access to the patient's nose and mouth through gaps/openings in this partial face mask housing. Cushioning elements and face mask rim are also shown.
Figure 15:
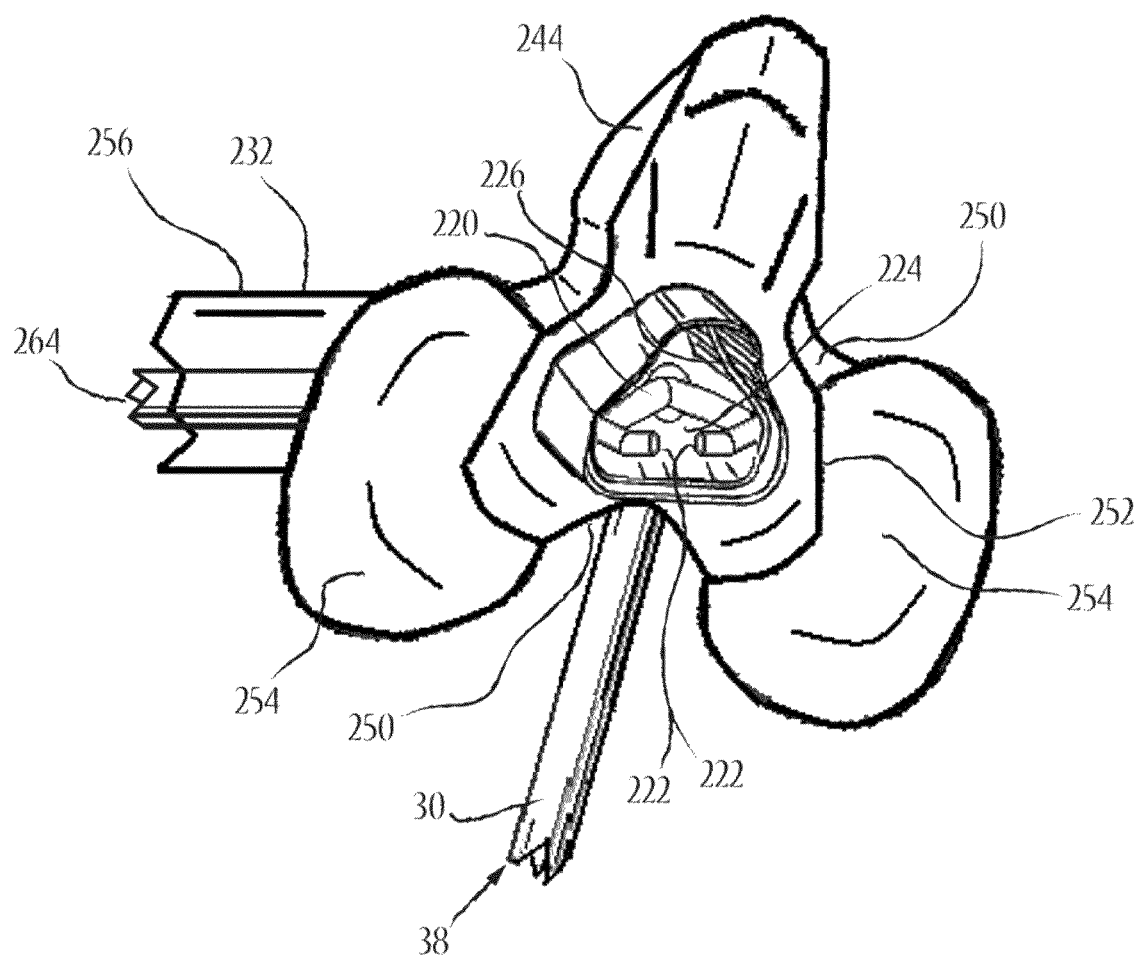
FIG. 15 is the partial face mask housing and dampening disperser as in FIG. 11, but with a boom that holds the dampening disperser in place, in the vicinity of the patient's nose and mouth, instead of straps. Not shown is that the support boom is further attached to head gear and/or neck gear as the patient interface. The boom can further support a gas sampling line that can connect to a monitoring device to determine the concentration of gases in the vicinity of the patient's nose and mouth, such as exhaled carbon dioxide.
Figure 16:
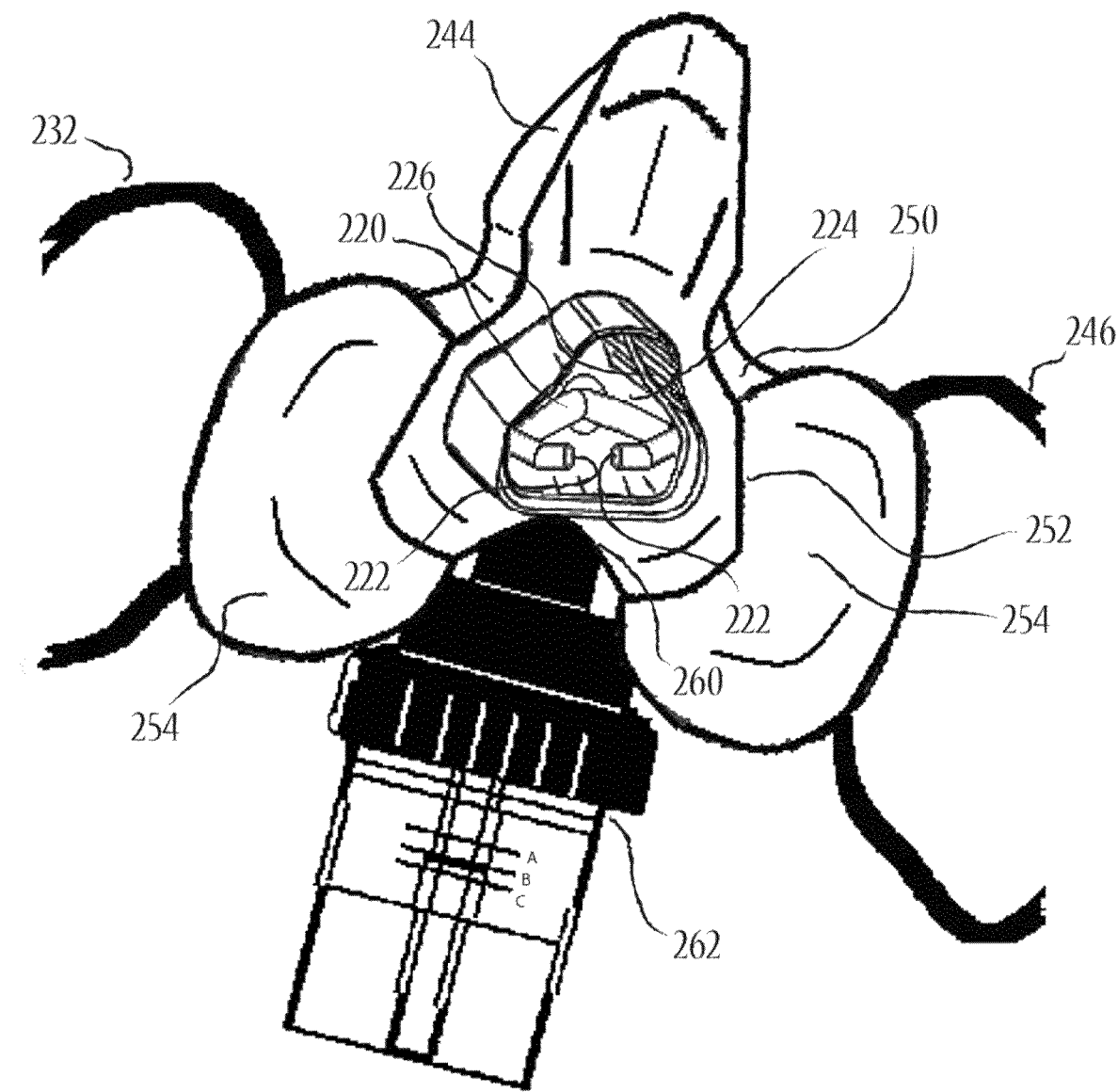
FIG. 16 is the partial face mask housing and dampening disperser as in FIG. 11, but further includes a nebulizer attached to an aerosol port for the administration of nebulizer treatments of medicament. The partial face mask housing directs the aerosol to a region in the vicinity of the patient's nose and mouth, without directing aerosol toward the patient's eyes.

In the third preferred embodiments, as shown in FIG. 14, the least one dampening disperser 220 is configured to be supported in a position in front of a patient's face. The dampening disperser 220 includes or serves as at least some concave walls 226 of an at least a partial face mask housing 244. The at least partial face mask housing 244 includes at least one fastener 246 to hold the face mask 244 in place on the patient's face. The face mask shown does not form an airtight seal between the mask and the patient's face. In this manner, at least some ambient air can enter and at least some dispensed gas and exhaled breath can exit. The space 228 is in the vicinity of the patient's nose and mouth. The movement of airflow 248 to and from the space in the vicinity of the patient's nose and mouth can be accomplished by at least one vent, aperture, cutaway, or gap 250 of the mask, which can prevent pressure build-up in the system. In preferred embodiments, this gap 250 can allow access to the patient's mouth and nose, such as for suctioning, performing spirometry, incentive spirometry, peak flow and other types of respiratory care and oral care. The patient is able to speak with less hindrance during treatment. The patient is able to drink through a straw during treatment. There is reduced probability of aspiration. A naso-gastric intubation tubing may be accommodated for feeding and medicinal administration. In this manner, the patient's feeling of claustrophobia is abated patient comfort is improved.

In these third alternate embodiments FIG. 14, the at least partial face mask housing 244 includes at least one fastener 246 to hold the face mask 244 in place on the patient's face. The face mask housing contains a rim 252 for at least some contact with the patient's face so as to support the positioning of the dampening disperser in the vicinity of the patient's nose and mouth. The rim is further preferably comprised of at least one cushioning element 254 for both patient comfort and also to elevate the dampening disperser at least some distance from the patient's face. The rim, or its cushioning, can be chosen from cushioning elements including, but not limited to, pads, thick elastomeric pads, fabric pads, gel containing pads, liquid containing pads, wax pads, wax-filled pads, silicone-filled pads, air-filled pads, balloons, air-filled skirts and any combination of one or more of these cushioning elements. Note that the air-filled skirts would utilize some of the gas dispensed from at least one gas outlet nozzle to fill the skirt to create a cushion of air which is ejected against the surface of the patient's face to create an "air cushion," similar to that which lifts a hovercraft. Inflation of this air cushion can indicate that medical gas is flowing through the system. The comfort pad may also be formable/adjustable to contour to the face and to help hold the mask in position. The streamlined face mask design reduces feelings of claustrophobia that patients often have with more cumbersome face masks.

In these third embodiments, at least one dampening disperser 220 is supported and held in position by an at least one support 232 chosen from a class of head associated supports selected from medical gas delivery supports including, but not limited to, fasteners, straps 246 (FIG. 11), bands, elastic bands, chin supports, glasses-like supports, over the ear supports, over the ear elastic bands, over the ear tubing supports, arms, booms 256 (FIG. 15) and elbow-like supports, etc. and can include at least one swivel element 258, chosen from a class of swivel elements including, but not limited to, ball joints, hollow cylindrical rod-like housings that contain another rod-like structure of smaller diameter inside of it and allowed to rotate within it and cylindrical rod-like structures able to turn freely within a support structure, along with means of preventing said swivel element from dissociating, chosen from such means including, but not limited to nuts, washers, pins and flanges.

In these third alternate embodiments, the at least at least some concave walls (226) of an at least a partial face mask housing (244) preferably form an at least a partial prism-like shape.

In these third alternate embodiments, the at least partial face mask housing 244 preferably includes at least one ambient air vent 250 chosen from a class of ambient air vents including, but not limited to, air vents that are non-adjustable, air vents that are adjustable, air vents that are filterable, air vents that are closeable, and air vents that are resealable.

Again, in these third alternate embodiments, the at least partial face mask housing 244 preferably includes an aerosol port 260 (FIG. 16) for attachment to a nebulizer 262. In this manner, the patient may also receive a nebulizer treatment while wearing the support of the dampening disperser. The airflow of the dampening disperser may direct aerosol flow to the nose and mouth of the patient and away from the patient's eyes, for a higher respirable dose of aerosol.

In these third alternate embodiments, the at least partial face mask housing 244 preferably includes a gas sampling tubing line 264 (FIG. 15) with inlet positioned in a space in the vicinity of the patient's nose and mouth and outlet connected to a gas monitoring device/sensor. The monitoring device monitors gas composition in this region, such as exhaled gases which may include determination of the carbon dioxide concentration and ratio of carbon dioxide to oxygen.

In these third alternate embodiments of the medical gas delivery system, the at least partial face mask housing 244 may also include a removable support adapter that can align the dampening disperser with an endotracheal tube for delivery of medical gas to an intubated patient.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An apparatus for coupling a medical gas utilizing device to a first medical gas source having an output end defining an inner bore and a threaded outer surface, the apparatus comprising:
    a connector having a first end defining a first opening, a second end defining a second opening, and an annular abutment at or extending from the second end, the connector defining an open cavity region extending from the first opening and surrounded by a side wall with a threaded interior surface adapted to couple with the threaded outer surface of the output end of the first medical gas source; and
    a bushing being insertable into the connector and having an input end configured to be at least partially received into the inner bore of the output end of the first medical gas source when the threaded interior surface of the connector is coupled with the threaded outer surface of the output end of the first medical gas source, the bushing further including a first annular flange configured to reside within the open cavity region of the connector and engage with the annular abutment of the connector to prevent the bushing from being separated from the connector when the threaded interior surface of the connector is coupled with the threaded outer surface of the output end of the first medical gas source, where the input end of the bushing is configured to be at least partially received within the inner bore of the output end of the first medical gas source when the bushing engages against the output end of the first medical gas source to provide an airtight coupling when the threaded interior surface of the connector is coupled with the threaded outer surface of the output end of the first medical gas source, and the connector being rotatable about the bushing, and
    the bushing includes a bore that is directed entirely through the bushing along a longitudinal axis of the bushing;
    wherein the input end of the bushing is configured to couple with a second medical gas source having a nipple outlet; and
    wherein the nipple outlet of the second medical gas source is configured to be received within the bore of the bushing.

2. The apparatus of claim 1, wherein the first opening of the connector has a first diameter and the second opening of the connector has a second diameter, the first diameter greater than the second diameter, and
    wherein the input end of the bushing has at least one of a ball shape, a semi-spherical shape, or a bowl shape.

3. The apparatus of claim 2, wherein the annular abutment of the connector is positioned at the second end and is defined by the second opening of the connector, and
    wherein the first annular flange of the bushing has a diameter less than the first diameter of the first opening of the connector and greater than the second diameter of the second opening of the connector.

4. The apparatus of claim 1, wherein the first opening of the connector has a first diameter and the annular abutment defines a third opening having an effective second diameter, the first diameter greater than the effective second diameter.

5. The apparatus of claim 4, wherein the annular abutment of the connector extends into the open cavity region from the second end, and wherein the first annular flange of the bushing has a diameter less than the first diameter of the first opening of the connector and greater than the effective second diameter of the third opening.

6. The apparatus of claim 5, wherein the annular abutment is angled non-perpendicular relative to an axis of rotation of the connector about the bushing.

7. The apparatus of claim 1, wherein the annular abutment of the connector includes one or more recesses to allow the connector to be pushed over the first annular flange of the bushing.

8. The apparatus of claim 1, wherein the bushing comprises a second annular flange which engages with the second end or annular abutment of the connector outside of the open cavity region of the connector while the first annular flange engages with the connector inside of the open cavity region, such that the connector is inhibited from sliding upwardly or downwardly along an axis of the bushing, the axis being an axis of rotation of the connector about the bushing.

9. The apparatus of claim 8, wherein the bushing comprises an annular groove positioned between the first and second annular flanges, the annular groove configured to receive a portion of the annular abutment of the connector, and wherein the second annular flange is angled relative to the axis of the bushing.

10. The apparatus of claim 8, wherein the first opening of the connector has a first diameter and the second opening of the connector has a second diameter, and wherein the second annular flange of the bushing has a diameter greater than the second diameter of the second opening of the connector.

11. The apparatus of claim 1, wherein at least the input end of the bushing comprises at least one of a polymer, polyethylene, or a plastic.

12. The apparatus of claim 1, further comprising at least one user gripping means on an exterior surface of the side wall of the connector, the gripping means including at least one of a groove, a fingertip indentation, a friction-causing rough surface, or three radially protruding flanges.

13. The apparatus of claim 1, further comprising a flexible elastomeric medical gas tubing having a first input end attached to the bushing.

14. The apparatus of claim 13, wherein the medical gas tubing further includes a second output end adapted to attach to the medical gas utilizing device.

15. The apparatus of claim 1, wherein the bushing is slidably insertable into the connector.

16. An apparatus for coupling a medical gas utilizing device to a first medical gas source having an output end defining an inner bore and a threaded outer surface, the apparatus comprising:
   a connector having a first end defining a first opening of a first diameter, a second end, and an annular abutment extending from the second end toward the first end and defining a second opening of a second diameter, the connector defining an open cavity region extending from the first opening and surrounded by a side wall with a threaded interior surface adapted to couple with the threaded outer surface of the output end of the first medical gas source; and
   a bushing being insertable into the connector and having an input end configured to be at least partially received into the inner bore of the output end of the first medical gas source when the threaded interior surface of the connector is coupled with the threaded outer surface of the output end of the first medical gas source, the bushing further including a first annular flange having a diameter less than the first diameter of the first opening and greater than the second diameter of the second opening and configured to reside within the open cavity region of the connector, where the input end of the bushing is configured to be at least partially received within the inner bore of the output end of the first medical gas source when the bushing engages against the output end of the first medical gas source to provide an airtight coupling when the threaded interior surface of the connector is coupled with the threaded outer surface of the output end of the first medical gas source, and the connector being rotatable about the bushing, and
   the bushing includes a bore that is directed entirely through the bushing along a longitudinal axis of the bushing, and
   an end of the bushing opposite the input end is configured to be directly connected to a flexible medical gas tube.

17. The apparatus of claim 16, wherein the annular abutment extends from the second end of the connector at a non-perpendicular angle relative to an axis of rotation of the connector about the bushing.

18. The apparatus of claim 16, wherein the annular abutment of the connector includes one or more recesses to allow the connector to be pushed over the first annular flange of the bushing.

19. The apparatus of claim 16, wherein the input end of the bushing is configured to couple with a second medical gas source having a nipple outlet.

20. The apparatus of claim 16, wherein the bushing is slidably insertable into the connector.

21. An apparatus for coupling a medical gas utilizing device to a first medical gas source having an output end defining an inner bore and an outer surface, the apparatus comprising:
   a connector having a first end defining a first opening of a first diameter, a second end, and an annular abutment extending from the second end toward the first end and defining a second opening of a second diameter, the connector defining an open cavity region extending from the first opening and surrounded by a side wall with an interior surface adapted to couple with the outer surface of the output end of the first medical gas source;
   a bushing being insertable into the connector and having an input end configured to be at least partially received into the inner bore of the output end of the first medical gas source when the connector is coupled with the outer surface of the output end of the first medical gas source, the bushing further including an annular flange having a diameter less than the first diameter of the first opening and greater than the second diameter of the second opening and configured to reside within the open cavity region of the connector, the connector being rotatable about the bushing;
   wherein the annular abutment of the connector includes one or more recesses to allow the connector to be pushed over the annular flange of the bushing,
   the bushing includes a bore that is directed entirely through the bushing along a longitudinal axis of the bushing, and
   an end of the bushing opposite the input end is configured to be directly connected to a flexible medical gas tube.

22. The apparatus of claim 21, wherein the input end of the bushing is configured to couple with a second medical gas source having a nipple outlet.

23. A gas delivery system comprising:
   a connector including a bore that defines a first opening and a second opening opposite the first opening;
   a bushing positioned within the bore, the bushing including a first flange that is positioned within the bore of the connector, the first flange being configured to engage with the connector to prevent the bushing from being separated from the connector,
   the connector is configured to threadingly engage an output end of a medical gas source at the bore of the connector,
   the connector is configured to rotate about the bushing while the connector is simultaneously blocked from sliding upwardly or downwardly along a longitudinal axis of the bushing to threadingly engage the output end of the medical gas source,
   the bushing includes a second flange positioned outside of the bore of the connector, the second flange being configured to contact the connector, and
   wherein the first flange contacts the connector while the second flange contacts the connector to simultaneously block the connector from sliding upwardly and downwardly along the longitudinal axis of the bushing.

24. The gas delivery system of claim 23, wherein the bore is a first bore, and
   wherein the bushing includes a second bore that is directed entirely through the bushing along a longitudinal axis of the bushing.

25. The gas delivery system of claim 24, wherein the bushing is configured to couple with a nipple outlet of a second medical gas source, and wherein the nipple outlet of a second medical gas source is configured to be received within the second bore of the bushing.

26. The gas delivery system of claim 23, wherein the connector includes four radially protruding flanges extending away from an exterior surface of the connector;
wherein the four radially protruding flanges assist a user to rotate the connector to couple the connector to the medical gas source.

27. The gas delivery system of claim 23, wherein an input end of the bushing is configured to abut against the medical gas source at an outlet of the medical gas source to provide an airtight coupling.

28. The gas delivery system of claim 27, wherein the input end of the bushing has at least one of a ball shape, a semi-spherical shape, or a bowl shape.

29. The gas delivery system of claim 27, wherein when the connector is screwed onto the medical gas source, the first flange is configured to contact the connector to hold the input end of the bushing against the medical gas source at the outlet of the medical gas source.

30. The gas delivery system of claim 23, wherein the first flange is not angled relative to the axis of the bushing, and
wherein the second flange is angled relative to the axis of the bushing.

31. The gas delivery system of claim 23, wherein the connector includes a track positioned below the first flange of the bushing,
wherein the connector rotates relative to the bushing at the track of the bushing, and
wherein the first flange prevents the connector from leaking gas.

32. The gas delivery system of claim 23, further comprising a seal positioned within the bore of the connector, the seal being configured to prevent leak of gas between the connector and the medical gas source.

33. The gas delivery system of claim 23, wherein
the connector is color coded or includes indicia to direct a user to the medical gas source.

34. The gas delivery system of claim 23, wherein the gas delivery system further comprises a tubing directly connected to an end of the bushing, and a light source to illuminate the tubing.

35. The gas delivery system of claim 23, wherein an end of the bushing is configured to be directly connected to a flexible tube.

36. The gas delivery system of claim 23, wherein the second flange is positioned outside of the connector.

* * * * *